(12) United States Patent
Shenderova et al.

(10) Patent No.: US 9,296,656 B2
(45) Date of Patent: Mar. 29, 2016

(54) UV PROTECTIVE COATINGS

(75) Inventors: Olga Alexander Shenderova, Raleigh, NC (US); Varvara P. Grichko, Raleigh, NC (US)

(73) Assignee: International Technology Center, Raleigh, NC (US)

(*) Notice: Subject to any disclaimer, the term of this patent is extended or adjusted under 35 U.S.C. 154(b) by 1731 days.

(21) Appl. No.: 11/990,948

(22) PCT Filed: Aug. 25, 2006

(86) PCT No.: PCT/US2006/033626
§ 371 (c)(1),
(2), (4) Date: Aug. 7, 2009

(87) PCT Pub. No.: WO2007/027655
PCT Pub. Date: Mar. 8, 2007

(65) Prior Publication Data
US 2009/0297828 A1    Dec. 3, 2009

Related U.S. Application Data

(63) Continuation-in-part of application No. 11/338,527, filed on Jan. 24, 2006, now Pat. No. 7,612,138, and a continuation-in-part of application No. 10/936,743, filed on Sep. 8, 2004, now Pat. No. 7,224,039.

(60) Provisional application No. 60/712,507, filed on Aug. 30, 2005, provisional application No. 60/646,783, filed on Jan. 25, 2005, provisional application No. 60/501,646, filed on Sep. 9, 2003.

(51) Int. Cl.
*B32B 5/16* (2006.01)
*C08K 3/04* (2006.01)
*C09C 1/44* (2006.01)
(Continued)

(52) U.S. Cl.
CPC . *C04B 26/02* (2013.01); *C09D 5/32* (2013.01); *C09D 7/1216* (2013.01); *C09D 7/1266* (2013.01); *C09D 7/1275* (2013.01); *C04B 2111/00482* (2013.01); *C04B 2111/2076* (2013.01); *C08K 3/04* (2013.01); *Y10T 428/25* (2015.01)

(58) Field of Classification Search
None
See application file for complete search history.

(56) References Cited

U.S. PATENT DOCUMENTS 4,799,963 A    1/1989  Basil et al.
5,593,783 A *  1/1997  Miller ........................... 428/408
(Continued)

FOREIGN PATENT DOCUMENTS

KR    2004-105096 A    12/2004

OTHER PUBLICATIONS

English translation of JP 2003-081768, Higuchi, Mar. 2003.*
(Continued)

*Primary Examiner* — Ronak Patel
(74) *Attorney, Agent, or Firm* — Miller Patent Services; Jerry Miller

(57) ABSTRACT

A surface coating, colorant, pigment or polymer composite preparation that provides resistance to degradation when exposed to at least some portion of ultraviolet radiation having wavelengths between approximately 190 and 400 nm is made up of a dispersion of an effective amount of diamond nanoparticles in a binding matrix, wherein at least a portion of the diamond nanoparticles have a size greater than about 60 nm so that the diamond particles provide ultraviolet radiation degradation resistance properties in the dispersion. This abstract is not to be considered limiting, since other embodiments may deviate from the features described in this abstract.

39 Claims, 11 Drawing Sheets

(51) Int. Cl.
  *C04B 26/02* (2006.01)
  *C09D 5/32* (2006.01)
  *C09D 7/12* (2006.01)
  *C04B 111/00* (2006.01)
  *C04B 111/20* (2006.01)

(56) References Cited

U.S. PATENT DOCUMENTS

| | | | |
|---|---|---|---|
| 6,264,859 | B1 | 7/2001 | Basil et al. |
| 6,287,889 | B1 * | 9/2001 | Miyake et al. ............... 438/105 |
| 6,455,442 | B1 | 9/2002 | Bauer et al. |
| 7,300,958 | B2 | 11/2007 | Kataoka et al. |
| 7,427,361 | B2 * | 9/2008 | Small et al. ............... 252/79.1 |
| 7,569,205 | B1 | 8/2009 | Hens et al. |
| 7,732,642 | B1 | 6/2010 | Tan et al. |
| 7,867,467 | B2 | 1/2011 | Dolmatov |
| 8,389,584 | B2 | 3/2013 | Petrov et al. |
| 8,389,587 | B2 | 3/2013 | Pan et al. |
| 8,389,619 | B1 | 3/2013 | Tan et al. |
| 2004/0202601 | A1 | 10/2004 | Wen et al. |
| 2005/0158549 | A1 | 7/2005 | Khabashesku et al. |

OTHER PUBLICATIONS

English Abstract of JP 2002-265968, Hamada et al., Sep. 2002.*
Patterned diamond particle films, Fox et al., Mar. 2000.*
International Search Report; Application No. PCT/US2006/033626; Filing Date: Aug. 25, 2006.
Written Opinion of the International Searching Authority; Application No. PCT/US2006/033626; Filing Date: Aug. 25, 2006.
Shenderova, Zhirnov and Brenner; "Carbon Nanostructures", in "Critical Reviews in Solid State and Materials Sciences", 27(314):227-356 CRC Press (2002).
Shenderova and McGuire; Chapter 7, "Types of Nanodiamonds" in the text "Ultrananocrystalline diamond: Synthesis, Properties and Applications", CRC Press, co-written by Dr. Shenderova and Dr. Gary McGuire, Editors Shenderova, Gruen, William Andrews Publisher; (2006).
V.V.Danilenko, O.A. Shenderova, Chapter 5: Advances in Synthesis of Nanodiamond Particles, in Ultrananocrystalline Diamond, 2nd Edition, Eds. O.Shenderova, D. Gruen, Elsevier, p. 153 and entire chapter—Author proof submitted and may have minor differences from actual published document (2012).

* cited by examiner

UV PROTECTIVE COATINGS

CROSS REFERENCE TO RELATED DOCUMENTS

This application is related to and claims priority benefit of Provisional Patent Application No. 60/712,507 filed Aug. 30, 2005 to Shenderova, et al.; and is a continuation-in-part of U.S. patent application Ser. No. 11/338,527, filed Jan. 24, 2006 to Kuznetsov et al., which claims priority benefit of U.S. Provisional Patent Application No. 60/646,783, filed Jan. 25, 2005; and is also a continuation-in-part of U.S. patent application Ser. No. 10/936,743, filed Sep. 8, 2004 to McGuire, et al., which claims priority benefit of U.S. Provisional Patent Application No. 60/501,646 filed Sep. 9, 2003. This application is also related to PCT Application No. PCT/US2006/033626, filed of even date herewith to Shenderova, et al. and designating the United States entitled "Nanodiamond UV Protectant Formulations". Each of the applications listed above are hereby incorporated by reference.

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

Many materials including natural materials such as wood and synthetic materials, such as plastics, rubbers, paints, varnishes, adhesives, sealants and the like need to be protected against photochemical degradation when used outdoors or otherwise exposed to ultraviolet radiation (UVR) from the sun or when in the presence of artificial UVR sources. Ultraviolet (UV) light can initiate chemical reactions in natural and synthetic materials and products, that result in discoloration and loss of chemical and physical properties. UV stabilizers are added to the material or a coating applied to the surface to reduce the photochemical degradation. The types of light or UV stabilizers currently used are UV absorbers that act by shielding the material from ultraviolet light or hindered amine (or amid) light stabilizers (HALS) that act by scavenging the radical intermediates formed in the photo-oxidation process. Often hindered amines and UV absorbers are used together to provide a level of stability which is higher than would be provided by using either type of stabilizer by itself. It has been reported that the most effective screeners are those with the highest and broadest absorbance in both the UVB (290-320 nm) and UVA (320-400 nm) ranges of the UV spectrum.

Currently both organic and inorganic UV screeners used in plastics, paints, varnishes and other materials are commercially available. Organic UV absorbers are used typically at 1 to 3% of binder solids, depending on coating thickness. Examples of organic UV absorbers include hydroxyphenyl-benzotriazol, benzophenone and hydroxyphenyl-triazine. In the case of very prolonged exposure to UV radiation (sunlight or light from artificial sources), however, organic UV absorbers slowly degrade and so lose their protective effect. The effects of weathering (humidity, high temperatures) and the like may cause a loss of UV absorber through diffusion and leaching.

Inorganic UV absorbers, such as, for example, titanium dioxide, cerium dioxide or zinc oxide do not photochemically degrade. Such inorganic particles have been used to provide more scratch-resistance and UV-protection in transparent coatings. The use of large alumina particles can cause the transparent coating to exhibit an undesirable hazy appearance. Because of the high surface area of titanium dioxide, cerium dioxide and zinc oxide nano-particles and the potential for photochemically induced reactions, there is possible photochemical damage and degradation of the organic matrix surrounding the inorganic UV absorbers. This can result in loss of adhesion between the coating and substrate. This degradation must then be addressed by, for example, using inorganic binders.

BRIEF DESCRIPTION OF THE DRAWINGS

Certain illustrative embodiments showing organization and method of operation, together with objects and advantages may be best understood by reference detailed description that follows taken in conjunction with the accompanying drawings in which.

DETAILED DESCRIPTION

Figure 1:
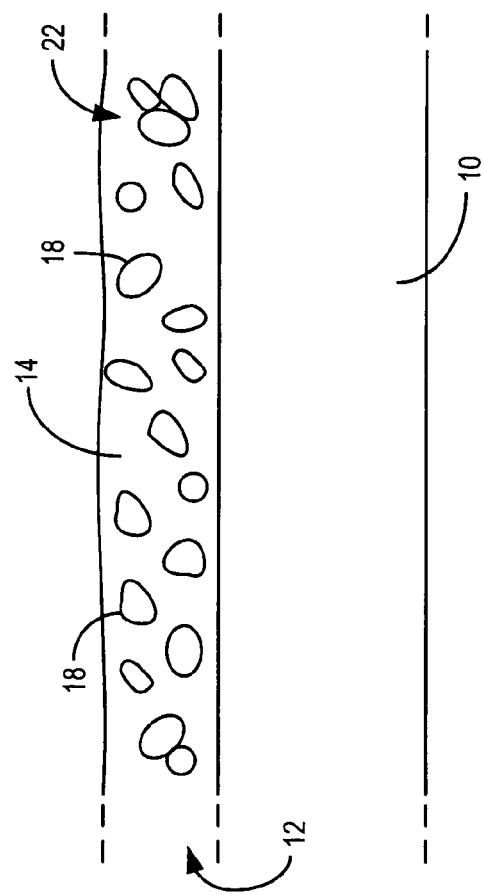
FIG. 1 is a diagram depicting a UV protecting coating applied to a substrate in a manner consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language).

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

For purposes of this document, the prefix "nano" as used, for example in "nanoparticle" is intended to refer to particles having length in at least one dimension in the range of approximately 1-1000 nanometers. However, in some particular cases, the length scale for achieving the novel properties and phenomena consistent with certain embodiments of the present invention may be less than 1 nanometer or be slightly larger than 1000 nanometers.

For purposes of this document, the terms UV absorbers, filters, sun blocks, UV protectants, UV screeners, UV attenuation, and the like will generally be used interchangeably without regard for any particular mechanism that causes the material to behave to protect against ultraviolet radiation, except in the context of a particular theorized mechanism that provides the exhibited characteristics. It will be recognized by those skilled in the art that various mechanisms may operate in such products to produce the desired effect including light reflection, dispersion, scattering, and absorption. Any presentation of theory of the UV protection mechanism is presented to explain the inventors' current understanding of the operational mechanism and is not to be considered limiting in any way, since at this writing such information may only constitute unproven theory.

As used herein, the term "binding matrix" or "binder" is defined as a substance within which the nanodiamonds are contained or suspended. In general, paints, primers, varnishes and other coatings involve three main constituents—binder, pigment and solvent. Diluants and various additives and fillers may also be used in many coating formulations in order to obtain a suitable viscosity and render additional properties of the additives to the coating. Although there is no pigment in most clear coatings and no solvent in some coatings designed to produce thick films, all three main constituents are commonly present in the different types of organic coatings. In some instances, actual binding of the particles may take place only after the binder is cured. Examples include, but are not limited to epoxies, paints (the term to include primers), resins, plastics or other polymer coatings. The term "cure" as used herein is used to refer to a drying, solidification or other curing or setting process. For example, a paint may cure by drying (evaporation of solvent), whereas an epoxy may cure by setting in accordance with a chemical bonding process. Generally, in the case of wet binding matrices, a cured matrix will also achieve a degree of dryness. However, certain binding matrices may be dry upon application (e.g., in a powder form) which cures by heat or other influences to form a coating without being in a wet or liquid state. In such cases, the term "binding" in "binding matrix" refers to the particles being bound upon curing.

Embodiments consistent with the present invention utilize nanoparticles of diamond. In order to understand this discussion, it is important to have an understanding of the accepted terminology that will be used herein when discussing particle size. The term "primary particle size" (PPS) is the size of a smallest primary structure in a system. This size distribution is typically rather narrow and depends on the particle synthesis conditions. Most suppliers of nanoparticles list only primary particle size in their product specification. This particle size is typically defined from x-ray diffraction pattern, Scanning-Electron Microscopy (SEM), High-Resolution Transmission-Electron Microscopy (HRTEM) images or calculated from Brunauer, Emmett and Teller (BET) surface area measurements. However, the primary particles can form aggregates or agglomerates due to their high surface energy or fabrication/processing conditions. The size of the aggregates is referred to as the "aggregate" or "agglomerate" size herein to clearly call out the distinction. The term "particle size" (PS) is used to generically refer to either PPS or agglomerate size or a size of a combination of agglomerates and primary particles.

Agglomerate size can be measured in a number of ways (e.g., SEM for dry powder forms or unimodal analysis of photon correlation spectroscopy data for relatively transparent solutions) and often can be tens or hundreds of times bigger than the PPS. For clarity "primary particle size" or "agglomerate size", will be explicitly called out when appropriate. The term nanodiamond (ND) or diamond nanoparticles is used for submicron sized particles and may include both or either primary particles and particles formed by agglomerates of the primary particles. The term nanodiamond can also include 1- and 2-dimensional diamond structures such as rods, wires, walls, sheets, flakes, etc. with smallest dimension less than 500 nm.

For purposes of this discussion, particle size and agglomerate size was measured in a variety of ways including using unimodal analysis of photon correlation spectroscopy data (in this case, by setting the spectrometer to provide output in the unimodal mode) for dispersions in relatively transparent liquids. This measurement technique is rapid and has been found to provide consistent measurements compared to other techniques, and thus, measurements presented herein are based upon such technique when relatively transparent liquids are analyzed, but other measurement techniques (e.g., SEM, HRTEM) will yield similar results and can also be used when such techniques are more suitable.

For purposes of the present discussion, the term "degradation" is intended to encompass all types of degradation of compositions resulting from exposure to UV radiation (including, but not limited to, color fading or bleaching, and/or loss of adhesion and/or loss of physical properties). Use of this term encompasses both the material that is used as a coating or polymer composite fabricated by means of vacuum forming, blow molding, injection molding, hot press molding, and extrusion to name a few, or a surface being treated with the coating or colorant. The term "coating" is used as a generic term for surface coatings and the term "colorant" is used to embrace dies, pigments, stains and the like used primarily to impart coloration.

In accordance with certain embodiments consistent with the present invention, nanodiamond (ND) particles are used to absorb, scatter, reflect or otherwise inhibit the transmission of UV radiation to and absorption by natural and synthetic materials such as wood, polymers, dyes and pigments (including dyes, pigments, binders, etc. forming a part of the coating). While all aspects of the mechanism for the absorption of UV by nanodiamond particles may not currently be fully understood, throughout this document various theoretical aspects of this action are interjected in order to better teach the various embodiments of the invention as currently understood. However, it is to be fully understood that such discussions of the theory as to why ND particles behave in this manner is not to be considered limiting on embodiments of the present invention. That is, the claimed inventions are not bound by any theory presented herein, and disclosures of theory should be considered just that—theory.

Nanodiamond UV absorption spectra depend on ND concentration and a number of physical and chemical properties of the ND particles such as particle size, physical state, composition, and surface chemical group. ND particles can be modified as a result of wet or gas phase chemical reaction(s), or chemical reactions induced photo-chemically, electrochemically, mechanochemically, or by means of a plasma, irradiation or sonic energy or other means to obtain ND particles with an enhanced ability to absorb, scatter and reduce UV radiation.

In certain embodiments consistent with the invention, compounds and methods are provided to develop a new class of UV protection compositions. In other embodiments, particular UV protection compositions are provided. More particularly, diamond nanoparticles are used to formulate UV protective compositions such as paints (including primers), shellacs, lacquers, enamels, colorants, varnishes, coatings, plastics, rubbers, glasses, fibers, photographic papers, waxes, greases, oils and other compositions.

For example, in accordance with certain embodiments, in plastics compositions diamond nanoparticles are used to formulate UV protective compositions for such substrates as polycarbonate and polycarbonate blends, polyesters, unsaturated polyesters, polyester fibers, polybutylene terephthalate (PBT), polyethyleneterephthalate (PET), acrylics, polyamides, polyamide fibers, polyacetal, polyurethanes, styrenics and other plastics and coatings. These plastics are commonly used in applications exposed to UV light such as interior and exterior automotive parts, lighting, sunglasses, sheet glazing, window glazing, lawn and garden equipment, business machine housings—computers, telephones, telecom equipment housing, packaging (soft drinks bottles), appliances, toys, signage, interior auto fabrics (e.g. seatbelts), sporting goods, sporting apparel, outdoor fabrics (awnings, flags, etc.), carpets, textiles, door and window hardware, boats, bathroom shower stalls, cultured marble, polymer concrete, adhesives, shoe soles, sealants, furniture cushioning, glass windows and other applications.

In certain embodiments consistent with the invention, compounds and methods are provided to develop a new class of coatings and their pigmented versions, paints, possessing UV protection property including solvent-based coatings—materials that contain or are soluble in organic solvents and water-based coatings—materials that dissolve in or are dispersed in water. Solvent-based coatings include, but are not limited to, oils and oil based paints, shellacs, varnishes, enamels and lacquers. Drying oils, obtained chiefly from vegetable sources, are examples of oils, with linseed oil and tung oil being among the most common. Other polymerizing oils are also used for protective coatings. Varnishes are clear resin-containing finishes that dry by reaction of the binder in combination, usually, with solvent evaporation. Varnishes are also produced with vehicles including oleoresinous binders, alkyd resins and urethane resins. Enamels are pigments dispersed in varnishes or resins that dry by reaction and not by solvent evaporation alone. Examples of enamel binders are the alkyds, the epoxies, the polyurethanes and the acrylics. Lacquers and shellacs are coatings in which the binder is dissolved in organic solvents and drying occurs solely by evaporation of the solvents. Examples of lacquers include vinyl and acrylic lacquers. Such materials are collectively referred to as "coatings" herein. This designation is without regard for the fact that such "coatings" often penetrate the surface of certain materials in use (e.g., oil coatings commonly soak into the surface of wood). By dispersing nanodiamonds in the corresponding vehicle for a coating, UV protection properties, or enhancement thereof, can be achieved.

In accordance with certain embodiments consistent with the present invention coatings containing nanodiamonds in a pure phase or dispersed in polymer matrix or other binding matrix can be used as UV protecting material.

FIG. 1 depicts a substrate 10 coated with an UV absorbing coating consistent with certain embodiments. In this illustration, substrate 10 is coated with coating 12 which is made up of a binding matrix 14 containing primary particles and/or agglomerates of tightly-bond nanodiamond particles (i.e., particles) such as 18 including at least two primary nanodiamond particles in the agglomerate. The binding matrix may also carry aggregates of loosely-bond diamond particles such as those depicted as 22, in certain embodiments. The coating 12 may be a polymer matrix such as polymethylmethacrylate (PMMA), polytetrafluorethelyne (PTFE)), polycarbonate, polystyrene, polyurethane, polyimide, acrylics, a paint or epoxy coating, or resin, etc. and can be applied to the substrate using any number of techniques. Use of nanodiamond is intended for both protecting the substrate 10 from UV damage as well as to protect dyes, pigments or binder within the coating 12 from bleaching and photodegradation in certain embodiments of the invention.

In certain embodiments, a coating containing nanodiamond particles can be applied either on an outer or inner surface of a UV transparent free standing support structure such, as for example window glass, providing UV protection of the interiors behind the support (for example, interior of a house or an automobile and other embodiments) on the side opposite to the source of UV radiation. Similar, nanodiamond particles can be incorporated to such support structure or be enclosed between two support structures.

Molded polymer composites with nanodiamonds can be used without a special substrate, in order to form housings, covers, containers or enclosures. Different methods of curing (such as thermal curing, for example) can be used to form free-standing structures (e.g., molded parts) with UV protection properties.

Candidates for use as the binding matrix also include, but are not limited to: elastomers, methacrylic, phenolic, vinyl, silicone, polyester, polyurethane foam (PUF), PDMS (polydimethylsiloxane), conducting polymers, vinyl polymers, phenol formaldehyde, neoprene, rubber, silicone rubber compounds, polypyrrole, polyaniline, polyacetylene, polythiophene, poly-p-phenylene, polyacrylthiophene, poly-p-phenylene-benzo-biz-thiozole (PBT), butadieneacrylonitrile, fibers, ceramics (e.g., SiO2, Al2O3), conductive polyethylenes (CPE), polyethyelene compounds with polyisobutylene, ethylene ethyl acrylate copolymers, extruded polystyrene foam (e.g., Styrofoam™), and expanded polyvinylchloride (e.g., Spongex™), to name but a few examples.

The selection of the polymer matrix is not believed to be critical, and the specific application will generally dictate which binding matrix is used. For any matrix the nanodiamond particles should preferably, but not necessarily, be uniformly or near uniformly dispersed in the binding matrix.

As a mechanism of fabrication of coatings containing nanodiamond particles dispersed in a polymer matrix, different techniques can be used that include, for example, dipping, roller coating, brushing, spray techniques, fluidized bed, spin-on coating of a polymer suspension and wiping to mention just a few. The spray techniques include paint spray, electrostatic spray, hot melt spray, high velocity high temperature spray, thermal spray, plasma spray, and ultrasonic spray. Spray techniques may be a practical way to synthesize coatings on large free-standing surfaces. Using different spray technique the coatings incorporated nanodiamonds can be applied over large free-standing surfaces (e.g., an aircraft body), in applications for protection of civilian or military aircraft, ships or other transportation vehicles or structures.

Figure 2:
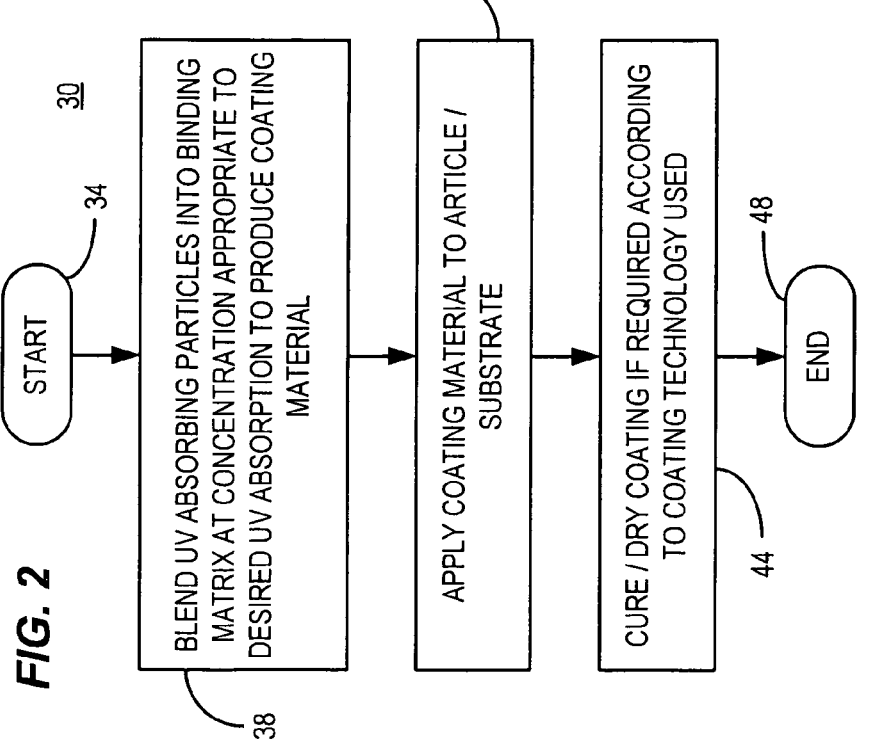
FIG. 2 is a generalized flow chart depicting a coating process consistent with certain embodiments of the present invention.

FIG. 2 generally shows a process 30 for both manufacture of the coating material and application of the coating starting at 34. At 38, operative quantities of nanodiamond particles, which may be functionalized or processed with any of the above variations, are blended into the binding matrix which serves as a carrier and binder for the nanodiamond particles. The concentration of nanodiamonds can be determined experimentally to achieve a desired degree of UV absorption, as will be described in connection with the experiments that follow, but may generally be in the range of 0.1-25.0% by weight or more preferably in the range of 0.5-5.0% by weight.

At 42, the coating can be applied to the article to be coated (i.e., the substrate—which may, for example be a panel of an aircraft or automotive part or a part of a building or other construction). Any of a number of application processes is appropriate for this process. If required, depending upon the binding matrix, the coating can then be cured or dried at 44, depending upon the technology used.

The curing process 44 may be a negligible part of certain processes while in other processes curing may be a more extensive and may involve, for example, application of heat or exposure to cure accelerants or other catalysts.

In an alternative embodiment, rather than applying the coating to an article or substrate at 42, the blend can be molded or otherwise fashioned into a free-standing article (e.g., a molded transportation vehicle part) at 42. In either event, the process ends at 48.

Use of diamond particles for UV protection can be very beneficial. Bulk diamond has a refractive index of approximately 2.4. Thus diamond particles scatter light very efficiently. Such diamond particles have been discovered to be strong absorbers of UVB and UVA radiation, as well as UVC radiation. Thus, ND particles provide a single physical absorber of UVA, UVB and UVC radiation to avoid the complications connected with processing of a UVR protection composition when combining different type of particles or organic absorbers (which does not preclude use of such additives to further enhance the UV protective qualities of a given composition).

While a complete understanding of the strong absorption in UV spectra of radiation by nanodiamond particles is yet to be revealed, possible mechanisms theorized for causing the absorption include absorption by the atoms with $sp^2$ bonding terminating a part of the particles surfaces; the surface groups involving other elements in addition to carbon; and absorption by internal defects in the bulk of diamond particles followed by photoluminescence and other phenomena. For example, there are several defect centers due to dopant atoms (N, B and other elements), self-interstitials, vacancies, complexes of the above, complexes of the charged defects, dislocations that cause absorption and photoluminescence, particularly at wavelengths shorter than 420 nm. That means that UV light is absorbed by these structural features and then is reemitted at a longer wavelength, primarily in the visible range of light for the case of photoluminescence.

While the fundamental absorption edge of bulk diamond is at a wavelength of about 220 nm (the band-gap of diamond is 5.5 eV), there are reports of effective band gaps in ultradispersed diamond particles within the range of ~3 eV. Dopants, surface states, internal defects and atomically sharp grain boundaries observed between primary diamond particles are all believed to contribute to the formation of the sub-bands within a fundamental band gap and thus cause the UV absorption at wavelengths longer than those corresponding to the fundamental band-gap.

The photoluminescence and other processes of conversion of absorbed UV radiation into emitted light in diamond particles are believed to be possibly due to defects that are present naturally as a result of material formation/processing or created by subsequent irradiation (for example, electron, ion or other types of irradiation) or obtained by subsequent annealing or be created by other means. In accordance with certain embodiments, diamond particles that actively absorb UVC, UVB, and UVA radiation can be used in UV protection compositions for paints, lacquers, varnishes, plastics and the like with sunscreen attributes alone or in combination with other UV filters.

There are also other benefits of using diamond particles as UV filters. Diamond particles possess a chemically inert core that provides additional benefits for its use in UV protection compositions in outdoor and indoor use. ND is resistant to moisture and acid and basic environments. ND is thermally resistant and may add to coatings other useful properties such as increased degradation temperature and improved flammability, increased adhesion, improved resistance to wear, scratch resistance, durability and the like. This can be a significant advantage in certain applications when compared to other UV filters. UV light that is still getting through the coating generates free radicals that can cause the coating material degradation. Since diamond nanoparticles are reported to scavenge free radicals a further benefit may be obtained in protecting coatings and structures from being damaged or bleached as a result of UV-induced radical chain reactions. The surface of the diamond particles can be easily functionalized with a very broad variety of different chemical functional groups that can facilitate dispersion of diamond particles in different compositions.

Nanodiamond particles can be utilized in a number of ways, for example:

in a method of protecting a surface or material from ultraviolet radiation by applying to the surface or material a formulation including an acceptable solvent or carrier and nanodiamonds or a mixture of nanodiamonds with other organic and inorganic UV absorbers, light stabilizers, antioxidant agents and other additives;

in a method of protecting a surface from ultraviolet radiation by topically applying to the surface a formulation having an acceptable solvent or carrier, a paint, a polish, a dye, or a coating material containing nanodiamonds or a mixture of nanodiamonds with other organic and inorganic UV absorbers, light stabilizers, antioxidant agents and other additives;

in a method of protecting a surface or an object from ultraviolet and other radiation by introducing an aerosol containing nanodiamonds or a mixture of nanodiamonds with other organic or inorganic UV absorbers or gaseous carrier containing nanodiamonds or a mixture of nanodiamonds with other organic or inorganic UV absorbers, light stabilizers, antioxidant agents and other additives;

in a method of protecting a material by incorporating nanodiamonds or a mixture of nanodiamonds with other organic or inorganic UV absorbers, light stabilizers, antioxidant agents and other additives in structures formed by molding, extrusion or other similar means;

in a method of protecting a material by incorporating nanodiamonds or a mixture of nanodiamonds with other organic or inorganic UV absorbers, light stabilizers, antioxidant agents and other additives in a surface layer of a structure formed by molding, extrusion or other similar means.

Diamond nanoparticles can be produced by several means. Vapor phase formation such as chemical vapor deposition, ion irradiation of graphite, chlorination of carbides, and techniques using shock wave energies are some of the several possible methods to produce such diamond particles. It should be mentioned that besides diamond particles of spherical form or irregular-shaped particles other 1- and 2-dimensional nanodiamond structures had been fabricated such as ND rods, wires, walls, sheets, flakes, etc. which can also be used in UV protecting compositions (on methods of synthesis of these structures see O, Shenderova and G. McGuire, Types of Nanodiamonds, book chapter in "Ultrananocrystalline diamond: Synthesis, Properties and Applications", Editors: O, Shenderova, D. Gruen, William-Andrews Publisher, 2006).

The shock wave method of nanodiamond particle production includes graphite transformation by a shock wave (the primary particle size for most popular current commercial products produced by this method is about 25 nm) and nanodiamond produced by detonation of carbon-containing explosives (the primary particle size produced by this method is approximately 3-5 nm in most currently available commercial products). Primary nanodiamond particles produced by detonation of carbon containing explosives form both tightly bonded aggregates (possibly fused during the detonation process) and loosely bonded aggregates.

As will be described with reference to various publications below, which are hereby incorporated by reference, diamond nanoparticles can be produced by several means, and which will result in varying primary particle sizes and varying agglomeration characteristics (see O. Shenderova and G. McGuire, Types of Nanodiamonds, book chapter in "Ultrananocrystalline diamond: Synthesis, Properties and Applications", Editors: O. Shenderova, D. Gruen, William-Andrews Publisher, 2006). Isolated nanocrystalline diamond particles with characteristic sizes of several tens of nanometers can be monocrystalline or polycrystalline. Monocrystalline particles are obtained by processing of micron-sized diamond particles, which are, in turn, a byproduct of natural diamond or synthetic high pressure high temperature (HPHT) diamond synthesis. Synthetic diamond particles with sizes below ~50 microns represent the raw material for making micron and sub-micron diamond size particles.

The processing of micron sized diamond particles to smaller fractions includes micronizing, purification and grading of the powder. The polycrystalline nanodiamond powder can be processed from micron sized polycrystalline diamond particles obtained by shock wave synthesis. Under suitable conditions, explosively produced shock waves can create high pressure-high temperature conditions in confined volumes for a sufficient duration to achieve partial conversion of graphite into nanometer-sized diamond grains (~20 nm) which compact into micron-sized, polycrystalline particles. The processing of micron sized diamond particles to smaller fractions includes micronizing, purification and grading of the powder. For example, polycrystalline or monocrystalline nanodiamond particles described above are sold by Microdiamant AG, Switzerland. Range of particle sizes provided by Microdiamant include the smallest fraction sizes 0-50 nm (median size: ~25 nm), 0-100 nm (median size 50 nm), 0-150 nm (median size 75 nm) and larger fractions of polycrystalline diamond. For monocrystalline natural diamond particles the size ranges include 0-250 nm (average size 125 nm) fraction and larger size fractions. Frenklach and co-workers [Frenklach M, Kematick R, Huang D, et al., Homogeneous nucleation of diamond powder in the gas phase, *J. Appl. Phys* 66, 395-399, 1989] studied nucleation and growth of nanodiamond powder directly in the vapor phase in a substrate-free low-pressure microwave-plasma chemical vapor deposition (CVD) reactor. The particles were collected downstream of the reaction zone on a filter within the tubular flow reactor and subjected to wet oxidation to remove non-diamond carbon. The homogeneous diamond nucleation took place when a dichloromethane- and trichloroethylene-oxygen mixture was used as source material. The particles had crystalline shapes with an average particle size of around 50 nm. A mixture of diamond polytypes were observed in the powder. Frenklach et al. [Frenklach M., Howard W., Huang D., et al., Induced nucleation of diamond powder. Appl. Phys. Lett., 59, 546, 1991.] also studied the effects of heteroatom addition on the nucleation of solid carbon in a low-pressure plasma reactor. The addition of diborane ($B_2H_6$) resulted in substantial production of diamond particles, 5 to 450 nm in diameter, under the same conditions that show no diamond formation without the presence of diborane. Recently, spherical, rather monodispersed diamond particles with diameters of different fractions in the range from 150 to 600 nm have been synthesized in the gas phase by multi-cathode direct current plasma activated CVD [Lee J K, Baik Y J, Eun K Y, et al., Synthesis of diamond spheres Chem. Vap. Depos., 10, 133, 2004]. The internal structure of a spherical particle is made of nanocrystalline diamond grains ~30 nm in size. Other methods of nanodiamond formation include ion irradiation of graphite, chlorination of carbides, and several other possible methods to produce such diamond particles.

One of the most popular commercial nanodiamond products is nanodiamond produced by detonation of carbon-containing explosives (the primary particle size produced by this method is approximately 3-5 nm in most currently popular commercial products, although monocrystallite particle sizes up to 50 nm can be also observed). Primary nanodiamond particles produced by detonation of carbon containing explosives form both tightly bonded aggregates (possibly fused during the detonation process) and loosely bonded aggregates. Recently, using stirred-media milling technique, it was shown possible to de-agglomerate detonation nanodiamond down to their primary particle sizes, 4-5 nm. The slurries of 4-5 nm detonation nanodiamond particles can be resistant to agglomeration for a long period of time [A. Kruger, F. Kataoka, M. Ozawa, et al., Unusually tight aggregation in detonation nanodiamond: identification and disintegration, Carbon 43 (8),1722-1730, 2005]. As was mentioned above, different means of enhancement of UV absorption by different types of nanodiamond particles can be achieved. The above documents are hereby incorporated by reference herein. The nanodiamond produced by detonation of carbon-containing explosives have characteristics that have been documented in the above documents. Such nanodiamond is commonly referred to as "detonation nanodiamond", but are also equivalently called "ultrananocrystalline diamond particles", "ultradispersed diamond particles", and similar terms.

The experimental examples presented herein generally used agglomerates of detonation diamond nanoparticles, and the sizes presented are generally sizes of such nanoparticles. However, as noted above, primary particles of similar sizes are expected to perform in a similar manner. Hence, the present invention is not limited to agglomerates of smaller primary particles, but also encompasses use of larger primary particles than those of the detonation nanodiamond (DND) used in the experiments.

Commercially obtained nanodiamond powder produced by a detonation process, DND, is a polydispersed powder of particles mostly within the 10-1000 nm size range. These polydispersed nanodiamond particles can be fractionated into fractions with small and large particles with relatively narrow particle size distributions, with the size represented herein being measured using unimodal analysis of photon correlation spectroscopy data. These are the sizes of nanodiamond fractionated particles, largely aggregates that are used throughout this discussion unless otherwise designated. The sizes are measured by the photon correlation spectroscopy method when particles are dispersed in a liquid media or otherwise measured using SEM. The particle sizes referenced are thus a type of average values (assuming spherical shapes) of irregular shaped aggregate particles of diamond, as is conventional in this field. Examples of available nanodiamond fractionated particles include particles with 25 nm, 35 nm, 50 nm, 60 nm, 70-80 nm, 100 nm, 150 nm and larger particle sizes. Examples of fractionation approaches include centrifugation, ultracentrifugation, and density gradient centrifugation.

Based upon experiments conducted to date, there appears to be several advantages of using detonation nanodiamonds as UV filters (but this does not imply that nanodiamond produced by other means cannot be used). These particles demonstrate strong luminescence when excited by UV radiation, probably due to numerous internal defects formed during particle synthesis (nitrogen-related defects for example, since nitrogen is a constituent of the explosives used for the synthesis). Strong UV absorption can be also possibly attributed to the $sp^2$ termination of a part of a particle surface formed during subsequent particle processing. The particles contain a wide variety of surface chemical groups such as carboxyl, hydroxyl, amino, carbonyl and other groups some of which may contribute to the absorption.

Additionally it is noted that detonation nanodiamonds are intrinsically hydrophilic, thus they can form stable hydrosols. At the same time, some of them can be dispersed in a variety of alcohols, N-Methyl-2-Pyrrolidone (NMP) and oils (for example, nanodiamond purified with ozone) even without additional surface modification. Surface modification methods are also well developed for nanodiamonds to be dispersed in polar and non-polar media. For example, heat treatment of ND in air atmosphere at temperature 350-450° C. within an hour improves its dispersivity in water; surface fluorination in atmospheric plasma system using fluorine-containing gases helps improve dispersivity in acetone, chloroform, alcohols, tetrahydrofuran (THF) and some oils. Dispersion of nanodiamonds in different media can be done using ultrasonic energy, mixing, blending, shaking, magnetic stirring and other methods. Reduction of sizes of nanodiamond aggregates can be done by grinding, milling, treatment in atmospheric or subatmospheric pressure plasma and by other methods.

According to certain embodiments consistent with the present invention, a diamond particulate composition has UV attenuating diamond particles with a size greater than about 60 nm and generally less than about 1 micron. The composition can optionally further incorporate a composition of such particles in combination with other UV absorbing agents that can be chosen from organic screening agents, inorganic physical screening agents and their mixtures. The composition can comprise any UVA and UVB screening agent, which can be used in the coatings and plastics and by appropriate dispersion in an acceptable carrier such as a powder, oil, gel, wax, emulsion, solvent or other uncured coating or plastic base.

Sometimes, coatings and plastic products are preferably visually transparent or nearly so. Detonation diamond particles with size less than approximately 120-150 nm in diameter can provide the advantage of forming highly uniform dispersions with a relatively high translucency factor (at concentrations, for example in water ~0.1 mass %). In addition, nanodiamond particles might provide the advantage of requiring a smaller amount of particulate per unit of surface as compared to other UV attenuating materials to be protected from UV light to achieve the desired level of protection.

According to certain embodiments, UV protection compositions can be formulated to contain as-purified diamond particles, functionalized diamond particles or diamond particles with attached organic molecules that are made particularly suitable for use with the desirable carrier, agent or solvent (liquid, solid or aerosol, and etc.). The vehicle may be an aqueous solution, or a polar organic solvent, alcohol, e.g. ethanol or other polar-solvent; acetone, natural or synthetic oil; an oil-in-water emulsion; or a water-in-oil emulsion; or a wax; and the like.

In accordance with certain embodiments consistent with the present invention, nanodiamond-derived particles can be used as a UV absorber and photostabilizer, including nanodiamonds produced by detonation, shock wave, chemical vapor deposition (CVD), high-pressure-high-temperature (HPHT), and other methods. Besides particles, other primarily 1- and 2-dimensional nanodiamond structures such as ND rods, wires, walls, sheets, flakes, etc. can also be used in UV protecting compositions.

Nanodiamond particles can be, in addition, doped or modified chemically (wet chemistry, gas phase reactions, catalytic conversion), electrochemically, mechanochemically, sonochemically, photochemically, by exposure to radiation and beams, by oxidation, for example, with acids, oxygen or ozone, annealing in air or other gas atmospheres or with plasma treatment and other methods to enhance absorption of UV radiation by creating of structural defects, $sp^2$ bonded surface termination and surface functional groups attached to the ND surface by either covalent or non-covalent bonds. It is also possible to perform functionalization of diamond particulate in a gas plasma discharge.

Also, diamond particles can be modified to enhance the stability of their dispersions in a suitable carrier or liquid, provide chemical compatibility and assure surface adhesion of the coatings. In addition, diamond and other carbon-based particulate mixtures with nanodiamonds may form complexes with organic molecules to enhance UV light absorption.

The energy of the UV radiation absorbed by diamond particles may be converted into energy of chemical bonds, scattered, dissipated as heat or converted into energy of photoluminescence. The diamond nanoparticles actively scatter light as a function of condition, particle size and shape, wavelength, polarization state, and angle of incidence. This is expected to reduce the amount of absorbed energy converted to heat and may provide additional aesthetic effect by either contributing to the color or other visible characteristics of the coatings.

According to certain embodiments consistent with the present invention, a composition of a coating with aesthetic appeal has diamond particles exhibiting photoluminescence, fluorescence or phosphorescence under UV or other light due to the presence of nitrogen and other impurities defects, N-V centers or other structural features. The emitted light wavelength is determined by the intrinsic diamond particle properties, excitation light and properties of the coating composition.

According to certain embodiments of the present invention, the formulation of coatings and plastics can be augmented with diamond particles of a chosen color e.g., white, violet, brick or other colors alone or in combination with other coloring agents. Doping of ND to induce colored centers can be realized by several means including at the stage of detonation of the explosives used to produce the ND by the addition of materials to the explosives that induce color variations. Doping can be also induced by radiation and other means known in the art.

Experiments have been conducted with quantities of ND agglomerates as low as 0.01 wt. % which have exhibited substantial ultraviolet absorption. In commercial coatings and plastics, an addition of perhaps as low as 0.5 wt. % or even lower may provide beneficial enhancement to coatings and plastics for enhancement of UV protection. Further, addition of 1-2 wt. % or greater, perhaps as much as 3 wt. % to 5 wt. % could provide even higher benefits in protection against UV. In some applications as high as 10-25 wt. % or even higher is projected to be useful for providing high degrees of UV protection, although high concentrations may contribute to visibility of the ND particles. Of course, the appropriate concentration of ND or similar materials can be determined experimentally according to the base material and the desired effect. Systematic trials of varying percentages of ND blended uniformly as an admixture with the desired base material can be done to determine the amount needed to achieve the desired result for any given base material. Thus, the above ranges should be considered as a starting point for straightforward experimental determination of the concentration needed to achieve a desired result. In the case of ND particles used in paint pigments or other additives, the above percentages may be adjusted upward so as to produce a suitable final concentration of the finished product after addition of the additive.

As will be seen in the experimental data, there is a surprisingly strong change in the absorption of UVR in the longer UV wavelengths that is dependent upon the nanodiamond particle size. This dependency is non-linear and heretofore unreported. At lower particle sizes, the ultraviolet light absorption properties may go unnoticed, but as particle size increases above about 60 nm, the amount of UV absorption is observed to dramatically and surprisingly increase at the upper end of the wavelength by a large factor that appears to have an approximately exponential shape. Under laboratory test conditions, transmission of UV light at 350 nm wavelength has been found to decrease by a factor of 19 when the size of particle agglomerates is doubled from 50 nm to 100 nm (3.8% vs. 0.2% of transmitted radiation). Transmission of UV light at 400 nm wavelength has been found to decrease by a factor of 15.8 when the size of particle agglomerates is doubled from 50 nm to 100 nm (14.2% vs. 0.9%). Between 60 nm and 100 nm, the light transmission at 350 nm wavelength, transmission was decrease by a factor of 8.5 (1.7% vs. 0.2%), and at 400 nm wavelength, transmission was cut by a factor of 10 (9% vs. 0.9%)

As particle sizes increase to the range of 125 to 150 nm and beyond, the transmission of UV light is extremely highly attenuated, but the particle size is such that the composition may become more readily visible in higher concentrations and application thicknesses. Hence, preferred ranges of particle agglomerate sizes range from about 60 to about 150 nm, with a more preferred agglomerate size range from about 75 to about 125 nm, and about 100 nm being most preferred in formulations where transparency of the particles is desirable. Higher concentrations and larger particle sizes can be used when transparency is not an important consideration. Particle sizes of approximately 100 nm provide extremely good UV absorption while remaining transparent at relatively high concentrations, and are therefore considered approximately optimum for such applications.

In view of the above noted properties of ND, it appears that these materials can be used not only as efficient UV radiation absorbers, but also visible radiation absorbers. To enhance the ability of ND to absorb UV radiation ND can be combined with an appropriate carrier or other material. Examples of the carriers and materials include, but are not limited to, virtually any base medium used in known coatings and plastics. The precise quantity of ND to be used in such formulations can be readily determined experimentally based on the desired UV absorbing properties of the final product and its cost, and the effect of ND on color and/or clarity of the formulation. Based on the absorption spectra it can be seen that formulations that contain as little as 2% mass with a size of ND particles as added to the dispersion of about 60-100 nm shows very substantial beneficial UV absorption.

The ranges of values for the addition of ND particles given herein are to be considered as representative amounts provided as guidance to further refinement and experimentation and should not be considered absolutes or limiting. Additionally, the ranges listed herein are to be interpreted as including every possible smaller range within each range, and when minimum or maximum values are provided, they are intended to be effectively unbound at the opposite end of the range. It is additionally noted that the mechanism and medium used to create the dispersion can result in additional agglomeration into larger particles agglomerates and this should be taken into consideration when developing a formulation since both UV absorption and transparency or translucency will be affected.

EXAMPLES

In the examples described below, ND particles produced by explosives detonation are used to illustrate the usefulness of nanodiamond in applications for protection from UV radiation. Detonation nanodiamonds (DND) are synthesized at the high pressure-high temperature conditions achieved within the shock wave resulting from the detonation of carbon-containing explosives with a negative oxygen balance. In this method, diamond clusters are formed from carbon atoms contained within explosive molecules themselves, so only the explosive material is used as a precursor material. A wide variety of explosive materials can be used. One example of a typical explosive is a mixture of TNT (2-methyl-1,3,5-trinitrobenzene) and hexogen (hexahydro-1,3,5-trinitro-1,3,5-triazine) (RDX) composed of C, N, O and H with a negative oxygen balance (i.e. with the oxygen content lower than the stoichiometric value required to react with the carbon of the explosive), so that 'excess' carbon is present in the system.

The explosion takes place in an inert (non-oxidizing) to carbon gas medium that plays the role of a coolant and is either gas ($N_2$, $CO_2$, Ar or other medium under pressure) or ice (water), so called 'dry' or 'wet' synthesis, correspondingly. The product obtained by detonation, called detonation soot, contains the diamond nano-particles along with other carbon structures. A variety of techniques can be used to separate the ND phase from soot, for example, by oxidizing the non-diamond carbon. A typical average primary particle size of DND is within the size range of 3-5 nm. In the final product, DND powder, nano-diamond primary nano-particles form tightly and loosely bonded aggregates ranging in the largest dimension from several tens to several hundreds of nanometers and up to micrometers. Since as-received purified powders contain a wide variety of particle sizes, they are called polydispersed. Polydispersed powder can be separated into fractions with a narrower range of particle sizes by known methods (for example, by centrifugation).

In the examples presented below, several types of DND obtained from different vendors were used for the experiments. Some DND were produced in a chamber containing a gas medium as the coolant (Kr-b) and some types of DND were produced using an ice coating around the detonation charge (Ch St, Ch Oz).

Sample Kr-b was purchased from the Institute of Biophysics, Krasnoyarsk, Russia and was produced at Krasnoyarsk Research Center, Russia by explosion of TNT/RDX in a $CO_2$ atmosphere and acid-oxidized, washed with water, and dried. Then the sample was modified by a vendor. Modification is based on incorporation of $Na^+$ ions into the ND surface. This modification increases significantly the DND dispersivity and hydrosol stability.

Ch St and Ch Oz samples were synthesized from a mixture of TNT/RDX (40/60 wt. %) explosives using ice cooling media (purchased from "New Technologies", Chelyabinsk, Russia). Ch St ND was obtained by the detonation soot purification process using a mixture of sulfuric acid with chromic anhydride treatment, washed with water, and dried. Ch Oz ND was purified from the soot in an ozone-flow reactor ('dry' oxidation method). The average size of the primary particles for both samples was about 4 nm. Further modification of the Ch St sample was performed at the vendor site. Sample Ch St was additionally purified using ion-exchange resins, heat treated in an air atmosphere and fractionated by centrifugation down to 150 nm average particle size when dispersed in water and measured using photon correlation spectroscopy (PCS). This modified sample is called Ch I6 in the experiments below.

From several DND samples, fractions of smaller particle sizes were produced for selected experiments. First, the initial DND powder was dispersed in DI water using a custom made direct-immersion horn-type ultrasound sonicator with an output power of 100-400 W. Then, the DND hydrosol was centrifuged at 20° C. using a multipurpose refrigerated centrifuge (Thermo Electron Corporation) equipped with a 17.5-cm fixed angle rotor and 50-mL conical centrifuged tubes. Centrifugation time varied between 5 minutes and 50 minutes depending on the fraction size of interest. G-forces varied between 1,000 g and 25,000 g. DND particle size distributions in their hydrosols were measured by PCS using a Beckman-Coulter N5 submicron particle size analyzer.

The surface chemistry of the samples under investigation is very different due to different methods of purification and modification applied to the samples. TABLE 1 summarizes the content of surface groups of the samples studied using FTIR spectra. FTIR spectra were obtained with a Varian 7000e FTIR spectrometer in transmission mode with averaging over 500 spectra. A wide variety of surface groups is observed for the ND samples under study. The type of surface group influences the dispersivity of DND in different solvents and materials as well as their resistivity to agglomeration and sedimentation. For example, the most stable water and alcohol suspensions can be formed from Ch Oz, Kr-b, and Ch I6. Stable oil-based suspensions can be also formed based on these ND (for example using Ch Oz and Ch I6). Surface groups of the nanodiamonds can be changed by known reactions in order to improve their dispersivity and resistance to agglomeration and sedimentation in different polar and non-polar media.

The graphs illustrate absorbance ($A=\epsilon lC$, $\epsilon$—extinction coefficient, l—sample thickness C—concentration) as a function of wavelength in nanometers. Absorbance $A=\log_{10}(I_0/I)$, where $I_0$ and I are incident and transmitted intensity of the radiation at a given wavelength. Since transmittance $T=I/I_0$, $A=1$ corresponds to a case when only 10% of the radiation was transmitted; at $A=2$ incident radiation is reduced 100 times. Absorbance was measured with a Perkin-Elmer Lambda 35 UV-Vis spectrophotometer. Instrument settings were as follows: 190-1100 nm scan range, 480 nm/min scan speed, 1 nm data interval, 1 sec. cycle time, and 1 nm slit width. Lamp change-over wavelength was set at 326 nm. Liquid samples were measured by placing them in 1-cm quartz cells.

Example 1

In this series of experiments Ch I6 ND was used. The dependence of UVR absorbance on the concentration of ND in water was investigated. 8 mg of ND powder was dispersed in 8 ml of DI water using sonication for 5 min. Sonication was carried out using a sonicator equipped with a tapered titanium horn with a tip diameter of 3 mm (Cole-Parmer® 750-Watt Ultrasonic Homogenizer EW-04711-60, 20 kHz) that was directly immersed into the sample. The output power was 10 W, output intensity ~100 W/cm². The unimodal particle size distribution obtained using PCS (Beckman-Coulter N5 submicron particle size analyzer) device was 180 nm. Then the suspension was diluted in half several times so that the concentrations of the test samples were 0.1, 0.05, 0.025, 0.0125, 0.00625 and 0.003125 wt. % of DND. While ND suspensions at 0.1 wt % and 0.05 wt. % concentrations of ND were light and opaque, suspensions starting with 0.025 wt. % concentration were transparent and show opalescence that might be attractive for some aesthetic-related applications.

All samples were tested at the same conditions; the sample volume for absorption measurements was 4 ml. The UV-VIS spectra were recorded using as a reference a quartz cell filled with pure DI water. Pure DI water does not absorb significantly in the wavelength range 200-900 nm.

Figure 3:
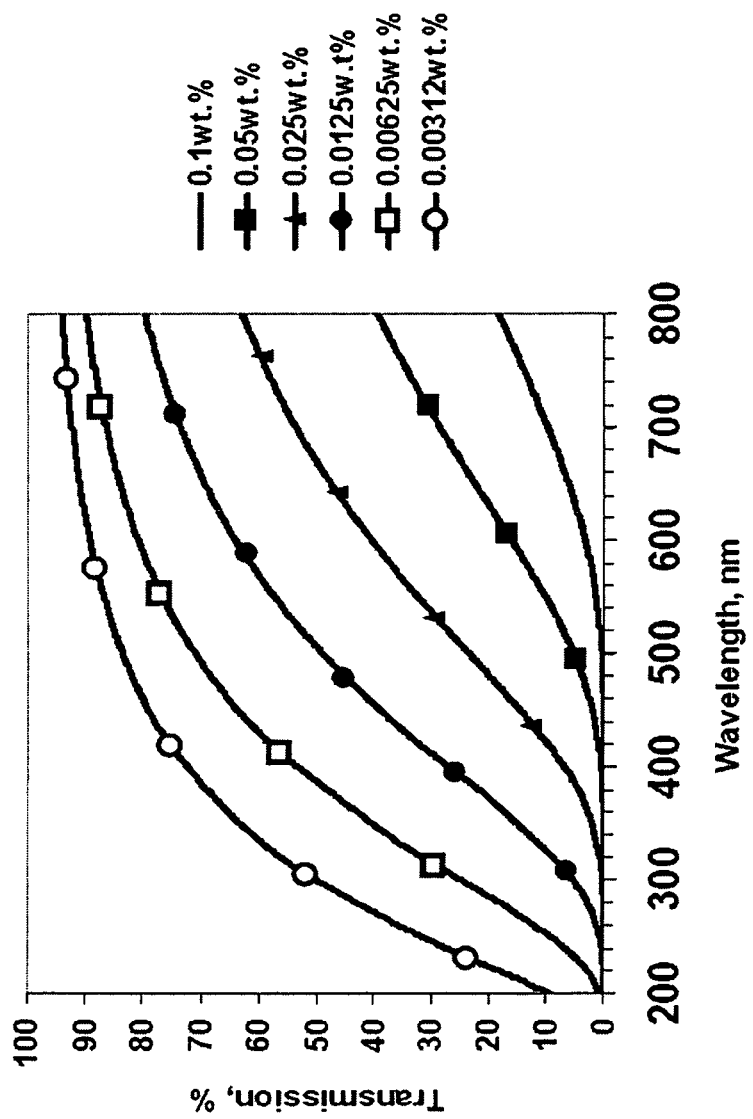
FIG. 3 illustrates the light transmission for Ch I6 nanodiamond (ND) dispersed in de-ionized (DI) water at six different concentrations starting with a 0.1 wt % ND suspension diluted in half for all subsequent measurements.

The recorded transmission spectra are illustrated in FIG. 3. As can be seen from the spectra, ND water suspension in the range of concentrations of 0.025-0.1 wt. % demonstrate strong absorbance of UVR (for example, transmission at 350 nm varies between 2.1% and 0.007% for the suspensions with 0.025 and 0.1 wt. % ND concentrations, correspondingly). Even suspensions with lower concentrations of ND such as 0.003125-0.0125 wt. % demonstrate reasonable UVR absorption (for example, transmission at 350 nm varies between 15% and 63% for the suspensions with 0.0125 and 0.003125 wt. % concentrations, correspondingly). Light absorption by ND suspensions is much stronger in the UV region than in the VIS region. For example, from the absorption spectra (not shown in the figure), absorbance at 300 nm wavelength is 6.4 times higher than at 600 mm. Also note the high transmission of the suspensions in the VIS region for samples with concentrations lower than 0.05 wt. %.

Example 2

In this series of experiments Ch St and Kr-b DND were used. The purpose of this experiment was to obtain DND water suspensions of large and small particles sizes at the same concentration by weight for comparison of their UV shielding. Ch St was surface-modified in order to improve its dispersivity in water. For this, Ch St powder was placed in an open glass container then heated at a rate of 10 degrees C./min up to 425° C. in an oven in air and then held at this temperature for 1 hour and then cooled down within an hour down to room temperature. This helped to obtain powder that disperses well in water, likely due to the increased amount of oxygen-containing surface groups. Then the sample was dispersed in DI water and fractionated using a centrifuge to obtain fractions with average aggregate sizes of 360 nm, 190 nm, 100 nm, 60 nm and 50 nm. Dried powders of the fractions 360 nm and 190 nm were obtained by evaporating the water. The smallest fractions of Ch St (100, 60 and 50 nm) were not dried to avoid possible agglomeration as a result of drying. Their concentrations were measured by first evaporating and weighing known volumes of the suspension. Once the sample concentration was known, it was easy to dilute a sample with a known concentration to the target concentration.

The Kr-B sample was also fractionated using the centrifuge to obtain 100 nm, 40 nm and 35 nm average aggregate size fractions. It is known that Kr-B fractions do not agglomerate during drying, so, dried powders of the 100 nm, 40 nm and 35 nm fractions of the Kr-B were obtained by the evaporating water. The smallest concentration of Ch St suspensions was 0.17 wt. % for 50 nm fractions. All other samples for UV-VIS spectral analysis were prepared at the same target 0.17 wt. % concentration by diluting 100 nm and 60 nm Ch St suspension or dissolving the necessary amount of dried powders of DND fractions in DI water. All suspensions were sonicated for 2 minutes. The sample preparation procedure for UV-VIS spectroscopic analysis is the same as in EXAMPLE 1.

Figure 4:
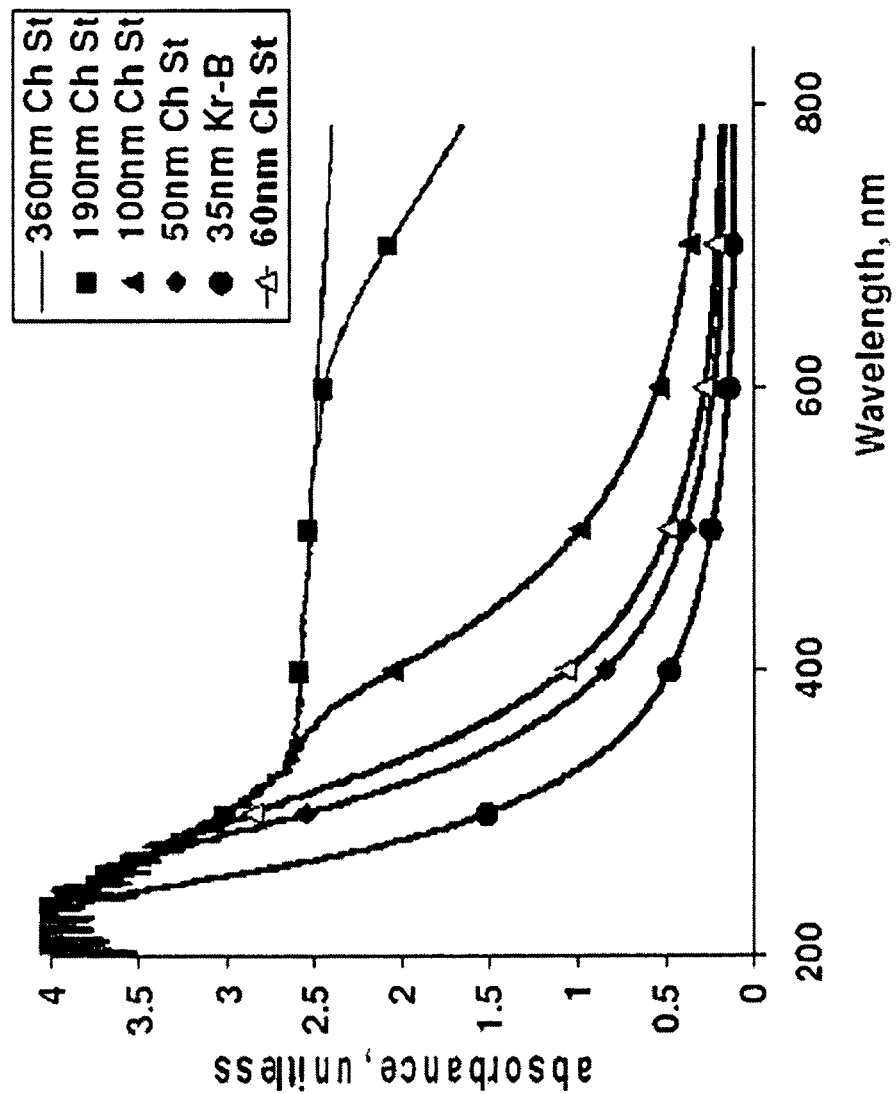
FIG. 4 illustrates UV-VIS (ultraviolet to visible) absorbance spectra of 0.17 wt % of fractions of different sizes for two types of nanodiamond particles (heat treated Ch St and Kr-b) dispersed in DI water.

Fractions 360 nm and 190 nm were light- and dark-grey, correspondingly. Suspensions of the fractions 100 nm and below were optically transparent, both 100 nm fractions for Ch St and Kr-B were brownish, 60, 50, 40 and 35 nm fractions showed a transition from light brownish to yellowish colors. The suspensions of the smallest fractions were more transparent. FIG. 4 illustrates the UV-VIS spectra for selected water suspensions of the fractions. Fractions 360 nm and 190 nm show large absorbance in both the UV and VIS spectra. Fractions 100 nm for both Ch St and Kr-B showed rather similar spectra (the latter was not included in FIG. 4), slightly larger absorbance was observed for the 100 nm Ch-St sample. According to FIG. 4, the most appealing for UV shielding compositions for transparent would be about 100 nm fractions, which demonstrate very high UV shielding in the range 200-400 nm, while possessing transparency in the VIS range. Larger agglomerates could be used where transparency is not a consideration.

Also, it can be noted that the curve corresponding to the suspension produced from the 100 nm Ch St sample is similar to the spectrum of the suspension produced using 100 nm Kr-b, (not shown in the Figure). It can be also noted an additional specific absorbance shoulder between 330 nm and 400 nm wavelengths which can be observed in FIG. 4 for 100 nm Ch St sample. This shoulder indicates additional UV absorption in this range. This can be due to the nitrogen defects since all samples contain up to 2.5 wt % of nitrogen.

Due to the rapid increase in UV absorbance when particle sizes are increased to 60 nm and above, these particles are believed particularly well suited for UV protection products for both UVA and UVB protection. This aspect is discussed further after discussion of all experiments. Note that all samples at all particle size demonstrate very high absorbance in a part 190-290 nm of UVC region (100-290 nm).

Figure 5:
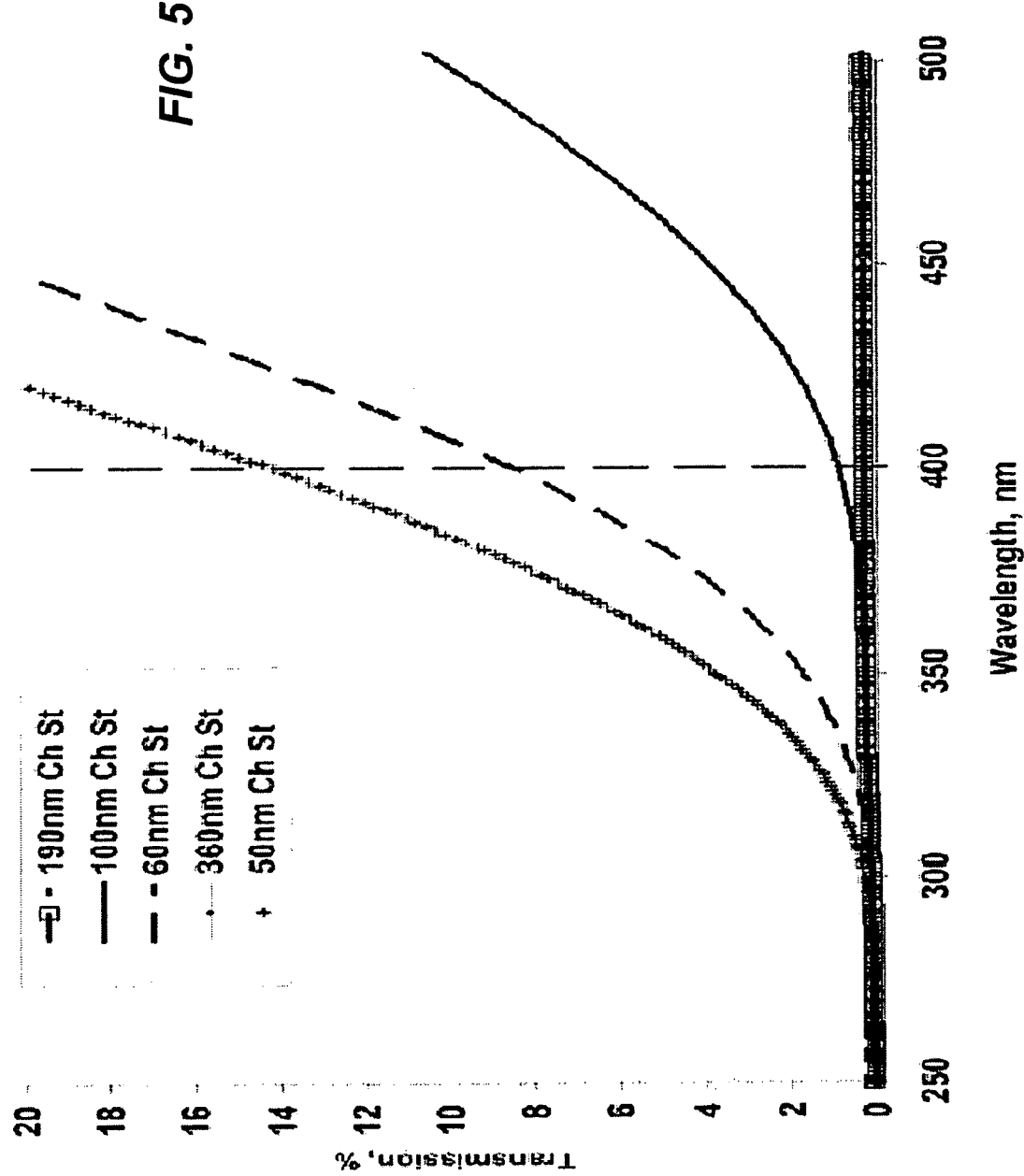
FIG. 5 illustrates UV-VIS transmission spectra of DI water containing 0.17 wt % nanodiamond prepared using fractions of different sizes for two types of nanodiamond particles (heat treated Ch St and Kr-b) dispersed using an ultrasonic horn.

FIG. 5 depicts transparency to UV radiation (rather than absorbance), and the scale was compressed to more readily see the dramatic change in UV absorption exhibited near the 400 nm range as a function of particle size. As a result of this experiment, it can be concluded that use of initial particle agglomerate sizes in the range of 60 to 150 nm can be used to substantially increase the UV attenuation without significant impact on visible transparency in relatively low concentrations of ND particles. When the visual presence of the particles is of secondary consideration, or used to augment pigmentation, even larger size particle agglomerates can be used to produce even greater UV absorption. It is noted that the particle agglomerate sizes may increase to varying degrees in formulating the product dispersion. This factor should be taken into consideration when determining how to formulate a UV protecting composition based upon the desired protection and visibility of the resulting product when in use. At this scale, the 190 and 360 nm particle agglomerate performance is too high to be readable on the graph, but is nonetheless shown for completeness.

Example 3

Figure 6:
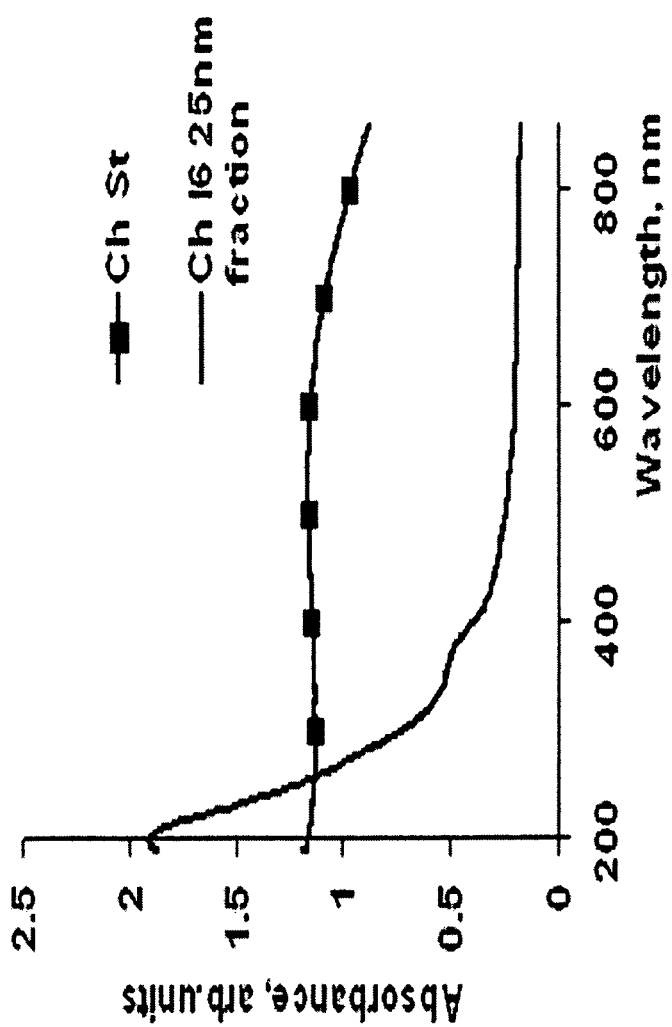
FIG. 6 illustrates UV-VIS absorbance spectra of nanodiamond films obtained by drying of nanodiamond water suspensions on quartz substrates. Suspensions of 250 nm Ch-St ND and 25 nm particle size fraction of Ch I6 sample were used for film preparation.

Dried films of DND were prepared on quartz substrates and their absorbance spectra were recorded. In this experiment, 0.8 ml of 1 wt % suspension of polydispersed Ch St ND in water was spread over the 4-cm$^2$ outer wall of a quartz cell and the water was slowly evaporated at room temperature. The resulting amount of DND in the film was 2 mg/cm$^2$. The film was grey and not transparent visually. In another experiment, a water suspension of 0.5 wt. % water suspension of a 25 nm fraction of Ch I6 nanodiamond was spread over a 3" quartz wafer (from Silicon West) placed on a hot plate at 120° C. The resulting dry ND film was visually transparent with a brownish hue. The resulting amount of DND in the film was 1 mg/cm$^2$. FIG. 6 illustrates the absorbance spectra of the two dried films. The grey non-transparent film prepared from DND suspension with relatively large aggregates using Ch St shows absorption that changes slightly over the entire UV-VIS region of the spectrum. Additional spectra for this film were taken after 3-hour sun exposure (afternoon, August in North Carolina). The two spectra were identical.

Despite the fact that the film made from 25 nm aggregate sizes of ND is very thin and transparent in the VIS region, absorption in UVA and, especially UVB and at shorter wave lengths is high (FIG. 6). Also, it can be noted from the figure that the specific absorption shoulder over the 340-420 nm wavelength range for the Ch I6 25 nm fraction (FIG. 6), that increases the UV absorption in this range, is present. This can be possibly due to the presence of nitrogen defects in the nanodiamond lattice. Thus thin ND film can be applied by different means for UV protection over different surfaces (wood, polymers, etc).

Example 4

Figure 7:
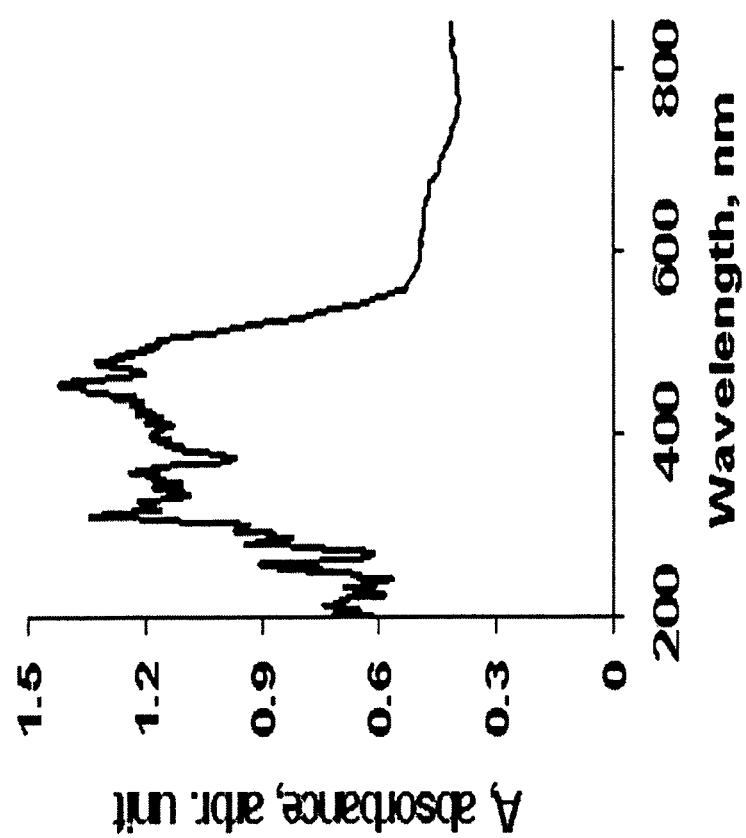
FIG. 7 illustrates the increase in the UV-VIS absorbance of yellow exterior acrylic paint (DuraCraft™) after the addition of 0.4 wt. % nanodiamonds to the un-dried paint. The spectrum was taken with reference to an identical sample without ND addition.

In this experiment 40 mg of Ch I6 powder was added to 10 g of Yellow exterior 100% acrylic flat house paint (DuraCraft™ brand paint was used). This resulted in 0.4 wt. % of ND in the un-dried paint. The ND powder was dispersed using magnetic stirring for 1 hr at 300 rpm. There was no visual difference between the initial paint and the paint with the ND addition. Then the initial paint and paint with ND addition were dispersed as a single layer using a foam brush over identical thin glass substrates resulting in approximately the same weight of paint. Three samples for each type were prepared. The samples were dried over a period of 2 days at room temperature. Then UV-VIS absorption spectra of the two types of samples were taken. FIG. 7 illustrates the typical increase in absorbance for all samples with the addition of ND to the paint as compared to the samples of the paint on glass without the addition of ND.

It is evident from this example, that ND particles can be introduced directly into the finished paint or other coating after formulation. Additionally, it appears that the ND particles could be introduced by way of direct introduction into the final product of ND particles in dry form, or mixed with a pigment, solvent or other additive during the manufacturing process or as a final step after packaging the product (e.g., at point of sale or use as a constituent of a pigment or other additive).

Example 5

Figure 8:
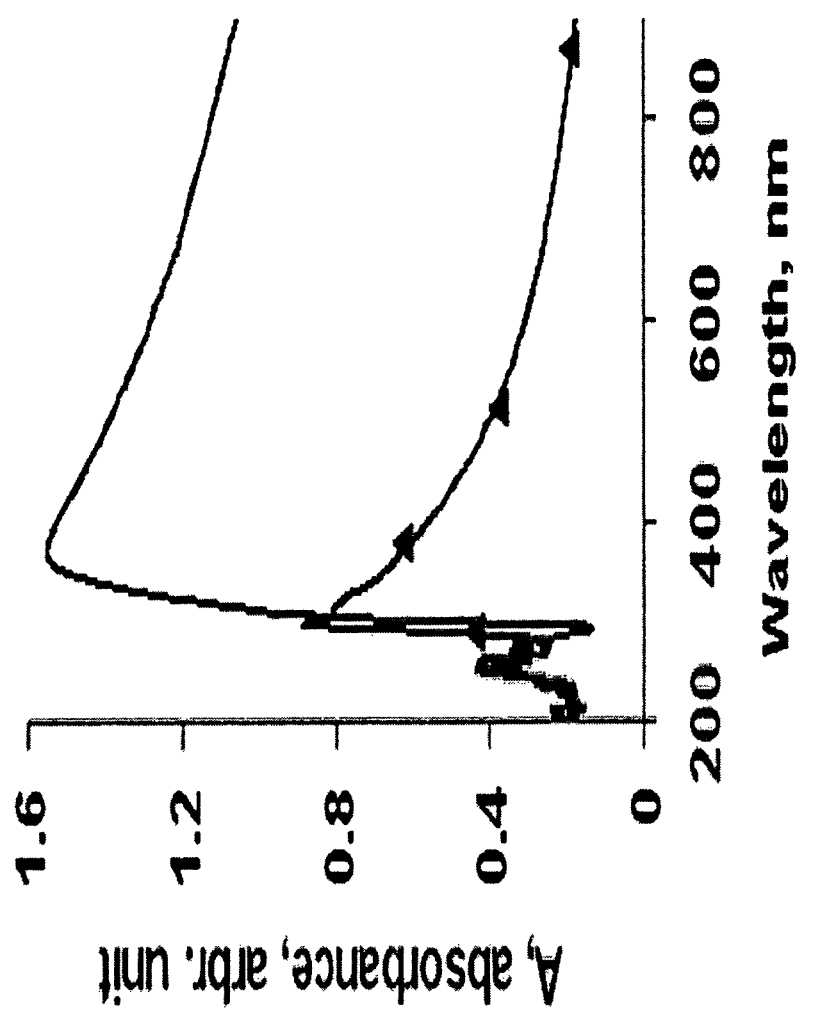
FIG. 8 illustrates the increase in the UV-VIS absorbance of a polyurethane Clear Satin finish after the addition of 1 wt. % (solid triangles) and 2 wt. % ND (solid line) to the un-dried finish. The spectra were taken with reference to an identical sample without ND addition. Ch I6 ND was used.

In this experiment 50 mg and 100 mg of Ch I6 powder was added to 5 g of MinWax™ brand Fast-Drying Polyurethane Clear Satin finish. This resulted in 1 wt. % and 2 wt. % of ND in the un-dried finish composition. The ND powder was dispersed using magnetic stirring for 1 hr at 300 rpm. Then the initial finish and the finish with the addition of ND were dispersed as a single layer using a foam brush over identical thin glass substrates resulting in approximately the same weight of finish. Samples in duplicate were prepared for both the finish with and without ND. The samples were dried over a period of 1 day at room temperature. Then UV-VIS absorption spectra for the samples with the two different ND concentrations were taken. The UV-VIS absorption spectrum of a sample of finish without the addition of ND was taken for comparison. FIG. 8 illustrates the increase in absorbance that was observed for all samples of Polyurethane Clear Satin finish after the addition of 1 wt. % and 2 wt. % nanodiamonds.

Again, it is evident from this example, that ND particles can be introduced directly into the finished polyurethane finish or other coating after formulation. Additionally, it appears that the ND particles could be introduced by way of direct introduction into the final product of ND particles in dry form, or mixed with a pigment, solvent or other additive during the manufacturing process or as a final step after packaging the product (e.g., at point of sale or point of use as a constituent of a pigment or other additive).

Example 6

Figure 9:
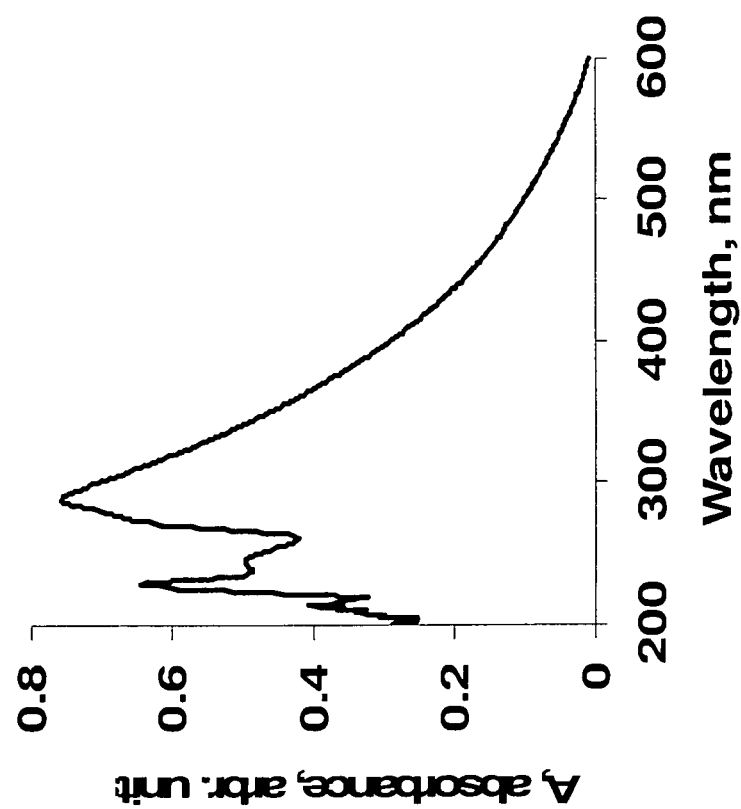
FIG. 9 illustrates the increase in the UV-VIS absorbance of water-based polyacrylic finish after the addition of a water dispersion of Ch Oz resulting in 4 wt. % of ND in the dried finish. The spectrum was taken with reference to an identical sample without ND addition.

In these experiments water-based polyacrylic protective finish Clear Satin (MinWax™ brand) was used. First, a water suspension of 2 wt. % Ch Oz powder was prepared by sonication of the suspension for a period of 10 min. Then 15 ml of the 2 wt. % ND water suspension was added to 15 ml of the protective finish. The suspension was stirred using magnetic stirring for 24 hrs at 300 rpm. For a control sample, 15 ml of pure water was added to 15 ml of the finish and stirred. Then the initial finish with just water added and the finish with ND suspension addition were dispersed as a single layer using a foam brush over identical thin glass substrates resulting in approximately the same weight of finish. Samples in duplicate of each were prepared. The samples were dried over a 1 day period at room temperature. The resulting ND content in the dried film was 4 wt. %. Then UV-VIS absorption spectra for the samples containing ND were taken and compared against the UV-VIS absorption spectrum a sample with pure finish with the addition of water without addition of ND. FIG. 9 illustrates the increase in absorbance of Water-based Polyacrylic protective finish after addition of ND suspension.

Again, it is evident from this example, that ND particles can be introduced directly into the finished polyacrylic finish or other coating after formulation. Additionally, it appears that the ND particles could be introduced by way of direct introduction into the final product of ND particles in dry form, or mixed with a pigment, solvent or other additive during the manufacturing process or as a final step after packaging the product (e.g., at point of sale or point of use as a constituent of a pigment or other additive).

Example 7

In these experiments Water-based Polyacrylic protective finish Clear Satin (MinWax™) with the addition of Ch Ox water suspension described in the example 8 was applied over eastern red cedar wood surfaces.

Figure 10:
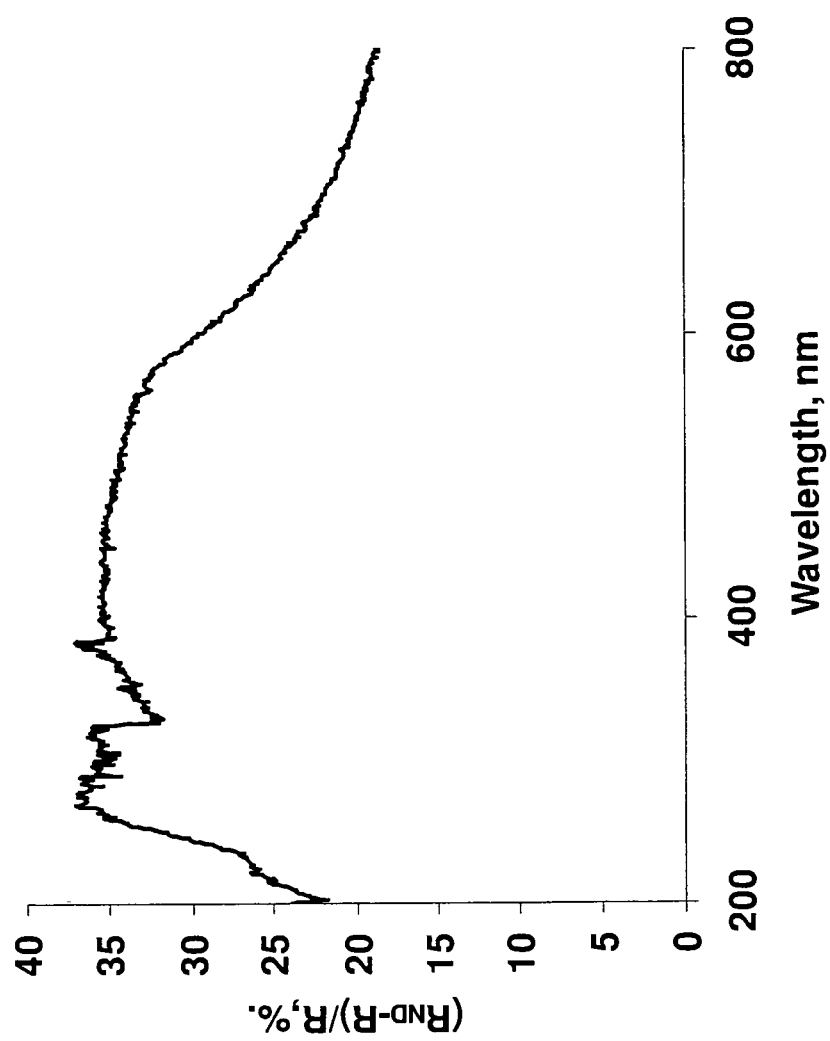
FIG. 10 illustrates the relative increase in the 45° UV-VIS reflectance of wood coated with polyacrylic finish containing 4 wt. % Ch Oz in the dried finish. The reflectance is compared with the spectra of an identical sample without ND addition.

Before the finish application, all bare wood samples were sanded with 150 grit paper then sanded with 220 grit paper in order to produce a smooth finish. A first coat was applied as a single layer using a foam brush over a wood substrate; in this case the Clear Satin finish was thinned 50% with water to allow maximum penetration. After the first layer was allowed to dry overnight, a second layer of the finish with and without ND were applied to different wood samples. Samples in duplicate were prepared. The samples were dried over a period of 2 days at room temperature. The resulting content of ND in the dried film was 4 wt. %. Since the wood samples were not transparent, UV-VIS reflection spectra of the finish surfaces were taken. FIG. 10 illustrates the relative increase in the 45° reflectance of wood coated with polyacrylic finish containing 4 wt. % Ch Oz ND in the dried finish as compared to the coating without ND. The increased reflectance in the UV region of the water-based polyacrylic protective finish after addition of ND reduces the penetration of the UV light through the coating and can therefore be concluded to improve wood protection from degradation due to UV radiation.

Again, it is evident from this example, that ND particles can be introduced directly into the finished polyacrylic finish or other coating after formulation. Additionally, it appears that the ND particles could be introduced by way of direct introduction into the final product of ND particles in dry form, or mixed with a pigment, solvent or other additive during the manufacturing process or as a final step after packaging the product (e.g., at point of sale or point of use as a constituent of a pigment or other additive).

Example 8

Several polyimid (PI) samples were fabricated with the addition of nanodiamond particles at different concentrations of Ch-St, Ch-Oz and Ch-Oz-B DND. ND powders were dispersed initially in N-Methylpyrrolidone (NMP) solvent, then sonicated for 5 min and mixed with commercial PI solution in NMP (PI-2611). PI-ND films were distributed over 3" diameter round glass substrates by the spin-on technique at 700 rpm for 45 sec. The samples were pre-baked in air for 120 sec at 120° C. on a hot plate. Then the samples were baked for 1 hr at 400° C. in a $N_2$ atmosphere. The sample thickness varied between 6-7 um over the substrates. The most stable NMP organosols with high dispersivity of ND particles were achieved using Ch-Oz, the ozone-treated nanodiamond powder, and especially its smaller fraction Ch-Oz-B. As small as 70 nm diamond particle sizes were achieved for NMP suspensions with several wt. % of Ch-Oz-B as measured by photon correlation spectroscopy (PCS) using a Beckman-Coulter N5 submicron particle size analyzer. ND-polyimid films were fabricated for all 3 types of ND at concentrations of 1 wt. %, 2 wt. % and 3 wt. % of ND in dried films.

Visually, the fabricated ND-PI nanocomposites were smooth and rather transparent, even at 3 wt. % of ND, preserving the yellowish color of pure PI samples. However, the transparency and overall appearance of nanocomposite films baked on 3" glass substrates varies depending on the type of ND used in the composite. These variations are believed to be due to different scattering of light by the nanoparticles of different sizes. While Ch-St samples with the largest particle size show some cloudiness, films with Ch-Oz are of high quality in terms of transparency, especially for the case of nanocomposite films prepared using the smallest fraction of Ch-Oz-B. Ch-Oz samples have a high concentration of oxygen-containing surface groups that probably enhance their dispersivity in NMP solvent. Thus it is believed that the type of surface groups on DND play a substantial role in dispersion of DND in particular solvents and the related polymer matrix. UV-VIS spectra indicate an increase in UV-VIS absorbance for all films containing nanodiamonds as compared to the pure polyimid film. The absorbance increased with increasing ND concentration.

Figure 11:
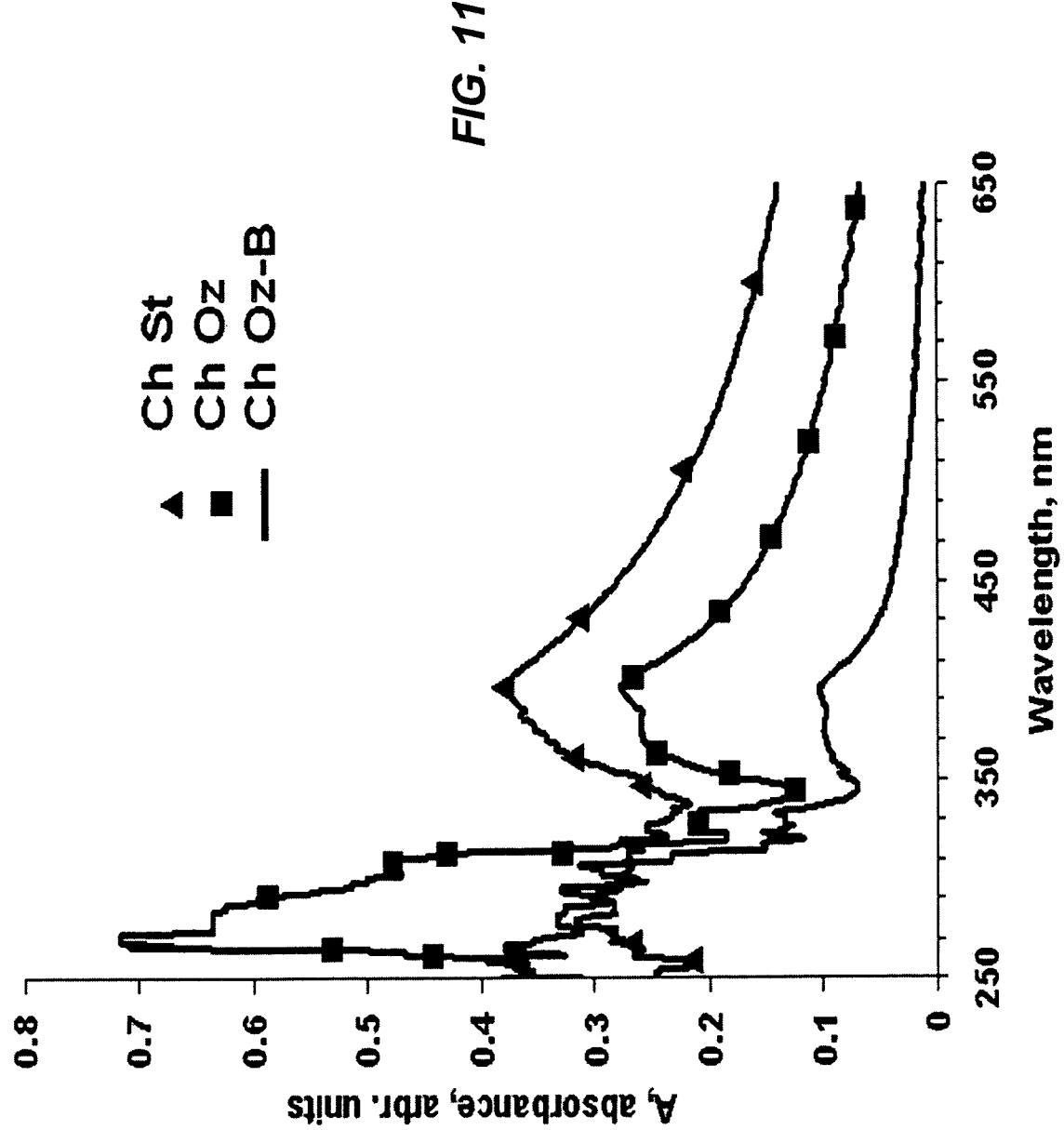
FIG. 11 illustrates the increase in the UV-VIS absorbance of polyimid films on glass substrates containing 3 wt. % of three different types Ch ND particles in the dried films. The spectra were taken with reference to an identical sample without ND addition.
Figure 12:
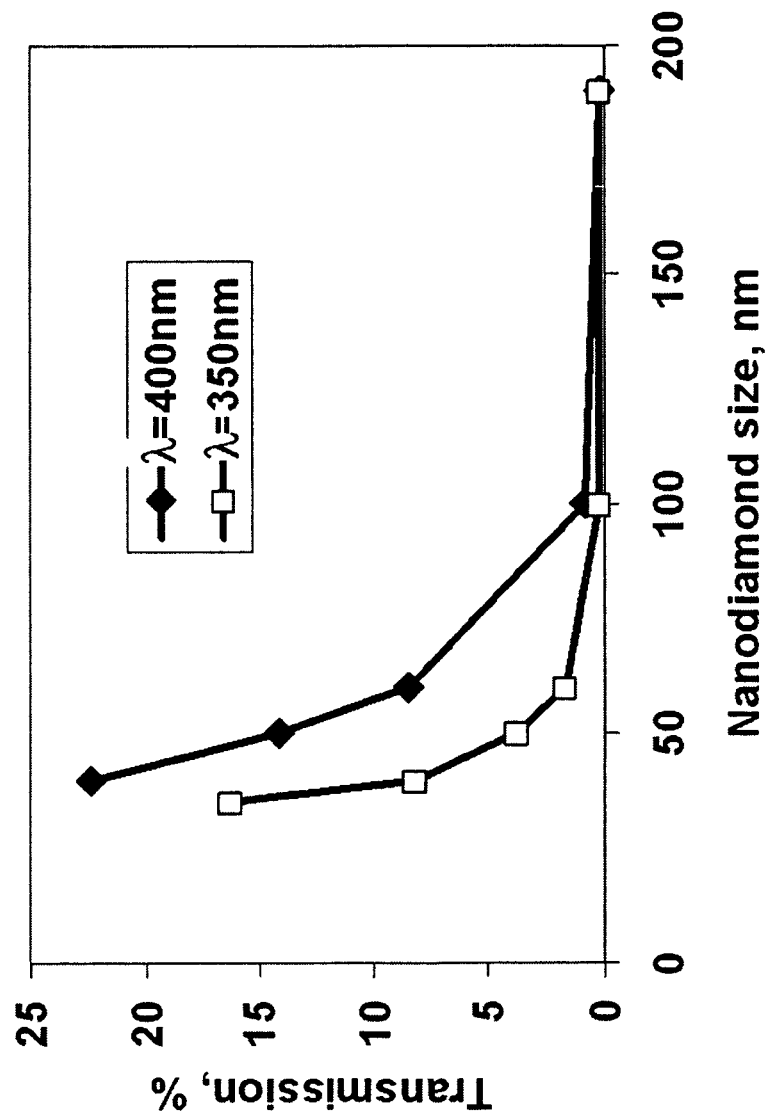
FIG. 12 illustrates light transmission as a function of agglomerate size at two particular wavelengths from the UV spectrum.

FIG. 11 illustrates the increase in absorbance for samples containing 3 wt % of nanodiamonds for Ch St, Ch Oz and Ch Oz-B ND.

Example 9

Nanodiamond films formed by drying ND suspensions on quartz substrates as described in EXAMPLE 4 were used in this series of experiments. The ND films confined between 2 quartz substrates were visually transparent with a brownish hue. This ND coated quartz structure was placed over several samples which otherwise lost their color quickly under sun exposure (July in North Carolina). As samples to demonstrate the protection from sun exposure provided by ND films, we used pink Post-It™ page markers (3M (670-5AF)). The page marker was covered in a way that part of it was covered by quartz coated with a ND film, part was covered with only pure quartz and part was open to air. After 2-days of sun exposure, visually there was a boundary between the more bright pink color preserved under the ND film and less colored part of the marker that was not protected with ND film.

Example 10

In this example 30 mg of red water-color paint (dry) was added to 2 ml of 0.2 wt. % of 40 nm average particle size of Ch I6 fraction suspended in DI water. Two milliliters of the paint was added to 2 ml of pure DI water. The paint was dissolved in the samples by shaking. Then two red lines were painted over white cotton fabric. A portion of both lines (control) was protected from the sun. The fabric was exposed to the sun for 2 weeks (July in North Carolina). In 2 days the color of the portion of the lines which was painted with only pure paint almost disappeared, while the red-brownish color of the line with the addition of ND lasted longer than 4 days. The water suspensions of the paint with and without ND in glass vials were also exposed to the sun. After one day the red color of the paint with no ND disappeared completely and a white residue was seen in the vile, while the red brick color of the paint water suspension containing ND was partially preserved even after 2 weeks of sun exposure.

Example 11

In this example Crayola™ kids' paint (dense liquid state) was used. The same amount of paint (pink, orange and green colors) was placed to glass vials and 2 ml of pure water and 2 ml of 0.08 wt. % of 60 nm average particle size fraction of Ch I6 ND were added. Samples were shaken and exposed to the sun for one week (July in North Carolina). In the case of the bottles with orange paint there was no visible change in the color of either the control sample or the sample with ND addition. For the bottles with pink and green paints there was visible bleaching of the color in the control samples while the colors of the samples with ND addition were much better preserved. The same paints were also dispersed above glossy paper and left for a week outdoors. Better color preservation was observed for samples with ND additions. In addition, samples with ND additions adhered better to the paper surface—after rain almost all paint without nanodiamond was removed from the paper while samples with nanodiamonds still covered approximately the original area.

From the above examples, it is evident that ND particles can be introduced into a colorant or coating product directly into the finished paint, varnish, polyurethane or other coating after formulation. Additionally, it appears clear that the ND particles could be introduced by way of direct introduction into the final product of ND particles in dry form, or mixed with a pigment, solvent or other additive during the manufacturing process or as a final step after packaging the product (e.g., at the point of use or at point of sale as a constituent of a pigment or other additive). When formulating an additive or pigment for later addition (e.g., addition of pigments during custom blending of paints, stains or varnishes), the concentration of ND particles should be adjusted to provide a suitable level of protection to the final product. Moreover, some pigments are more susceptible to deterioration in the presence of UV radiation. Hence, such pigments may be formulated with higher concentrations of nanodiamonds and/or larger nanodiamond particles than other pigments that are less susceptible to degradation from UV radiation. Generally, however, for additives or pigment products, the concentration of the ND particles might be higher than the proportions listed above in order to obtain a suitable concentration of the ND particles in the final product to provide the target level of UV protection. Furthermore, the ND particles can be introduced into the final product by virtue of initial dispersion into any suitable constituent of the final product including, but not limited to, a binder, a solvent, an additive, a pigment, a diluent, a filler, etc.

TABLE 1

FTIR analysis of the surface composition of the ND used in the present study.

| Chemical group | Ch St | Ch I6 | Ch Oz (same Ch Oz-Black) | Kr-b |
|---|---|---|---|---|
| O—H free, O—H, H bridge (OH) | 3573 cm$^{-1}$ weak | Shoulder 3590 cm$^{-1}$ | 3596 sh | 3588 sh |
| —NH$_2$, =NH, >NH | 3432 cm$^{-1}$ broad | 3432 cm$^{-1}$ broad | 3423 | 3410 |
| Above and - - - —CONH— —CONH$_2$— | — | — | — | 3245 sh |
| Methyl asym | 2960 cm$^{-1}$ very weak | — | 2960.1 | — |
| Methylene asym | 2930 cm$^{-1}$ weak | — | 2931 | 2927.9 |
| Methylene sym | 2858 cm$^{-1}$ very weak | — | 2859.5 | 2851.9 |
| R—C(=O)—O—C(=O)—R Satur | — | 1799 cm$^{-1}$ as well at 1289 cm$^{-1}$ | 1813.1 | 1773.9 |
| R—C(=O)—O—C(=O)—R unsatur | 1725 cm$^{-1}$ | — | — | — |
| —NH$_2$, >C=C< | 1631.6 cm$^{-1}$ | 1631.6 cm$^{-1}$ | 1628.0 | 1627.3 |
| R—C(=O)O— | — | — | — | — |
| H1a diamond feature, N—related (possibility) | — | Very weak shoulder 1460 cm$^{-1}$ | — | — |
| CH in CH$_3$, CH$_2$ | — | — | 1446.1 | 1448.4 |
| —CH$_3$, >C(CH$_3$)$_2$ | — | — | 1370.1 | — |
| >N—NO$_2$ | — | — | 1275.2 | 1319.6 sh |
| C—N=O | — | — | 1225.9 | 1210.5 |
| C—OH, adsorbed CO, CO$_2$ | 1120.2 cm$^{-1}$ medium | — | 1060.1 | — |
| >C=C(H)— | 802 cm$^{-1}$ extremely weak | — | — | 920.74 |
| 3 neighboring aromatic C—H | 781 cm$^{-1}$ extremely weak | — | — | — |
| C—H | 620 cm$^{-1}$ weak | — | 593.6 | 593.6 |

Thus, a surface coating, colorant, pigment or polymer composite consistent with certain embodiments that provides resistance to degradation when exposed to at least some portion of ultraviolet radiation having wavelengths between approximately 190 and 400 nm is made up of a dispersion of an effective amount of diamond nanoparticles in a binding matrix, wherein at least a portion of the diamond nanoparticles have a size greater than about 60 nm so that the diamond particles provide ultraviolet radiation degradation resistance properties in the dispersion.

In certain embodiments, the surface coating or colorant has a pigment that renders coloration to the surface coating or colorant. In certain embodiments, the surface coating or colorant has a solvent that is compatible with the binder. In certain embodiments, the surface coating or colorant has at least a portion of the diamond nanoparticles having a size of approximately 60-150 nm. In certain embodiments, at least a portion of the diamond nanoparticles have a size of approximately 100 nm. In certain embodiments, the diamond nanoparticles comprise up to 25.0 percent by weight of the surface coating or colorant. In certain embodiments, the nanoparticles comprise between about 0.5 and 5.0 percent by weight of the preparation. In certain embodiments, the nanodiamond particles have a visible color or are luminescent, and wherein the diamond nanoparticles impart a color to or modify a color of the dispersion. In certain embodiments, the surface coating or colorant is formulated as a paint, varnish, lacquer, enamel, polycarbonate and polycarbonate blends, polyester, polyester fibers, polybutylene terephthalate (PBT), acrylics, polyamide, polyamide fibers, polyacetal, polyesters, unsaturated polyesters, polyurethane, styrenics and other plastics and coatings. In certain embodiments, the diamond nanoparticles are modified as a result of wet or gas phase chemical reaction(s), or chemical reactions induced photochemically, electrochemically, mechanochemically, annealing, or by means of a plasma, irradiation or sonic energy to obtain diamond nanoparticles with an enhanced ability to absorb ultraviolet radiation. In certain embodiments, the binding matrix is selected from the group consisting of: a polymer matrix, an epoxy, polytetrafluoroethelyne, resins, polycarbonates and polycarbonate blends, polystyrene, polyurethanes, polyimides, acrylics, epoxies, methacrylic, phenolics, silicones, polyesters, polyester fibers, unsaturated polyesters, polyurethane foam (PUF), polybutylene terephthalate (PBT), polyamides, polyamide fibers, polyacetals, vinyl polymers, phenol formaldehyde, neoprene, rubber, silicone rubber compounds, polypyrroles, polyaniline, polyacetylenes, polythiophenes, poly-p-phenylenes, polyacrylthiophenes, poly-p-phenylene-benzo-biz-thiozole (PBT), polymethylmethacrylate, butadieneacrylonitrile, fibers, ceramics, glasses, polyethyelene compounds with polyisobutylene, ethylene ethyl acrylate copolymers, extruded polystyrene foam, and expanded polyvinylchloride and other plastics and coatings. In certain embodiments, the binding matrix containing the UV radiation attenuating nanodiamond particles is suitable for application as a coating to a substrate using at least one of an aerosol spray process, an electrostatic spray process, a hot melt spray process, a high velocity high temperature spray process, a thermal spray process, an ultrasonic spray process, a fluidized bed process, a dipping process, a brushing process, a spin-on process, a wipe-on process, a plasma spraying process, a casting process, a molding process and an injection molding process. In certain embodiments, an article is coated by the surface coating or colorant.

In another embodiment, a paint or surface coating preparation provides resistance to degradation when exposed to at least some portion of ultraviolet radiation having wavelengths between approximately 190 and 400 nm and includes a paint or surface coating preparation including a pigment, a binder, and a solvent that is compatible with the pigment and the binder; a dispersion of an effective amount of diamond nanoparticles in a paint or surface coating preparation; and wherein at least a portion of the diamond nanoparticles have a size greater than about 60 nm so that the diamond particles provide ultraviolet radiation degradation resistance properties in the dispersion.

In certain embodiments, at least a portion of the diamond nanoparticles have a size of approximately 60-150 nm. In certain embodiments, at least a portion of the diamond nanoparticles have a size of approximately 100 nm. In certain embodiments, the diamond nanoparticles comprise up to 25.0 percent by weight of the surface coating or colorant. In certain embodiments, the nanodiamond particles have a visible color, and wherein the diamond nanoparticles impart a color to or modify a color of the dispersion. In certain embodiments, the diamond nanoparticles are modified as a result of wet or gas phase chemical reaction(s), or chemical reactions induced photochemically, electrochemically, mechanochemically, annealing, or by means of a plasma, irradiation or sonic energy or modified during a process of nanodiamond synthesis by introducing dopants and defects to obtain diamond nanoparticles with an enhanced ability to absorb ultraviolet radiation. In certain embodiments, an article is coated by the paint or surface coating preparation.

In another embodiment, an ultraviolet radiation resistant structure provides resistance to degradation when exposed to at least some portion of ultraviolet radiation having wavelengths between approximately 190 and 400 nm and has a substrate with a layer of ultraviolet degradation resistant coating covering at least a portion of the substrate, wherein the ultraviolet radiation degradation resistant coating that includes an effective amount of diamond nanoparticles dispersed in a binder, wherein at least a portion of the diamond nanoparticles have a size greater than about 60 nm so that the diamond particles provide ultraviolet radiation degradation resistance properties in the dispersion.

In certain embodiments, a pigment renders coloration to the surface coating or colorant. In certain embodiments, a solvent that is compatible with the binder is used. In certain embodiments, at least a portion of the diamond nanoparticles have a size of approximately 60-150 nm. In certain embodiments, at least a portion of the diamond nanoparticles have a size of approximately 100 nm. In certain embodiments, the diamond nanoparticles comprise up to 25.0 percent by weight of the surface coating or colorant. In certain embodiments, the diamond nanoparticles comprise between about 0.5 and 5.0 percent by weight of the preparation. In certain embodiments, the nanodiamond particles have a visible color, and wherein the diamond nanoparticles impart a color to or modify a color of the dispersion. In certain embodiments, the diamond nanoparticles are modified as a result of wet or gas phase chemical reaction(s), or chemical reactions induced photochemically, electrochemically, mechanochemically, annealing, or by means of a plasma, irradiation or sonic energy or modified during the process of nanodiamond synthesis by introducing dopants and defects to obtain diamond nanoparticles with an enhanced ability to absorb ultraviolet radiation.

A pigment or additive to a surface coating or colorant preparation that provides resistance to degradation when exposed to at least some portion of ultraviolet radiation having wavelengths between approximately 190 and 400 nm, in accordance with certain embodiments has a dispersion of an effective amount of diamond nanoparticles in the pigment or additive, wherein at least a portion of the diamond nanoparticles have a size greater than about 60 nm so that the diamond particles provide ultraviolet radiation degradation resistance properties to the surface coating or colorant preparation when dispersed therein.

In certain embodiments, the pigment or additive has a solvent that is compatible with the pigment and the surface coating or colorant. In certain embodiments, at least a portion of the diamond nanoparticles have a size of approximately 60-150 nm. In certain embodiments, at least a portion of the diamond nanoparticles have a size of approximately 100 nm. In certain embodiments, the diamond nanoparticles comprise at least 0.1 percent by weight of the pigment. In certain embodiments, the nanodiamond particles have a visible color, and wherein the diamond nanoparticles impart a color to or modify a color of the pigment or additive dispersion. In certain embodiments, the diamond nanoparticles are modified as a result of wet or gas phase chemical reaction(s), or chemical reactions induced photochemically, electrochemically, mechanochemically, annealing, or by means of a plasma, irradiation or sonic energy or modified during the process of nanodiamond synthesis by introducing dopants and defects to obtain diamond nanoparticles with an enhanced ability to absorb ultraviolet radiation. A surface coating or colorant may contain the pigment or additive as a constituent thereof.

In accordance with certain embodiments, a method of imparting resistance to degradation due to exposure to ultraviolet radiation to a surface coating or colorant preparation when exposed to at least some portion of ultraviolet radiation having wavelengths between approximately 190 and 400 nm involves: providing an effective amount of diamond nanoparticles, wherein at least a portion of the diamond nanoparticles have a size greater than about 60 nm; providing a surface coating or colorant preparation; dispersing the nanodiamond particles into the surface coating or colorant preparation, so that the diamond particles provide ultraviolet radiation degradation resistance properties to the surface coating or colorant preparation when dispersed therein.

In certain embodiments, at least a portion of the diamond nanoparticles have a size of approximately 60-150 nm. In certain embodiments, at least a portion of the diamond nanoparticles have a size of approximately 100 nm. In certain embodiments, the diamond nanoparticles comprise at least 0.1 percent by weight of the surface coating or colorant. In certain embodiments, the nanodiamond particles have a visible color, and wherein the diamond nanoparticles impart a color to or modify a color of the surface coating or colorant. In certain embodiments, the diamond nanoparticles are modified as a result of wet or gas phase chemical reaction(s), or chemical reactions induced photochemically, electrochemically, mechanochemically, annealing or by means of a plasma, irradiation or sonic energy or modified during the process of nanodiamond synthesis by introducing dopants and defects to obtain diamond nanoparticles with an enhanced ability to absorb ultraviolet radiation.

A polymer composite material, consistent with certain embodiments, exhibiting resistance to degradation by exposure to at least some portion of ultraviolet radiation having wavelengths between approximately 190 and 400 nm has a dispersion of an effective amount of diamond nanoparticles in the polymer composite, wherein at least a portion of the diamond nanoparticles have a size greater than about 60 nm so that the diamond particles provide ultraviolet radiation degradation resistance properties to the polymer composite. In certain embodiments, the composite has a solvent that is compatible with the polymer composite. In certain embodiments, at least a portion of the diamond nanoparticles have a size of approximately 60-150 nm. In certain embodiments, at least a portion of the diamond nanoparticles have a size of approximately 100 nm. In certain embodiments, the diamond nanoparticles comprise at least 0.1 percent by weight of the polymer composite. In certain embodiments, the nanodiamond particles have a visible color, and wherein the diamond nanoparticles impart a color to or modify a color of the polymer composite. In certain embodiments, the diamond nanoparticles are modified as a result of wet or gas phase chemical reaction(s), or chemical reactions induced photochemically, electrochemically, mechanochemically, annealing or by means of a plasma, irradiation or sonic energy or modified during the process of nanodiamond synthesis by introducing dopants and defects to obtain diamond nanoparticles with an enhanced ability to absorb ultraviolet radiation. In certain embodiments, the composite is cured to a solid state. In certain embodiments, the polymer composite is applied to a UV transparent free standing support structure. In certain embodiments, the free standing support structure is glass. In certain embodiments, the polymer composite is sandwiched between two sheets of glass.

While certain illustrative embodiments have been described, it is evident that many alternatives, modifications, permutations and variations will become apparent to those skilled in the art in light of the foregoing description.

What is claimed is:

1. A surface coating or colorant preparation that provides resistance to degradation when exposed to at least some portion of ultraviolet radiation having wavelengths between approximately 190 and 400 nm comprising: a dispersion of an amount of diamond nanoparticles in a curable binding matrix, wherein a plurality of the diamond nanoparticles comprise ultradispersed diamond nanoparticles having a size greater than about 60 nm so that the diamond nanoparticles provide ultraviolet radiation degradation resistance properties in the dispersion.

2. The surface coating or colorant preparation according to claim 1, further comprising a pigment that renders coloration to the surface coating or colorant preparation.

3. The surface coating or colorant preparation according to claim 1, further comprising a solvent to the curable binding matrix.

4. The surface coating or colorant preparation according to claim 1, wherein of the plurality of diamond nanoparticles having size greater than about 60 nm have a size of approximately 60-150 nm.

5. The surface coating or colorant preparation according to claim 1, wherein the plurality of diamond nanoparticles having size greater than about 60 nn have a size of approximately 100 nm.

6. The surface coating or colorant preparation according to claim 1, wherein the diamond nanoparticles comprise up to 25.0 percent by weight of the surface coating or colorant.

7. The surface coating or colorant preparation according to claim 1, wherein the diamond nanoparticles comprise between about 0.5 and 5.0 percent by weight of the preparation.

8. The surface coating or colorant preparation according to claim 1, wherein the nanodiamond particles have a visible color or are luminescent, and wherein the diamond nanoparticles impart a color to or modify a color of the dispersion.

9. The surface coating or colorant preparation according to claim 1, formulated as a paint, varnish, lacquer, enamel, polycarbonate and polycarbonate blends, polyester, polyester fibers, polybutylene terephthalate (PBT), acrylics, polyamide, polyamide fibers, polyacetal, polyesters, unsaturated polyesters, polyurethane, or styrenics.

10. The surface coating or colorant preparation according to claim 1, wherein the diamond nanoparticles are modified as a result of wet or gas phase chemical reaction(s), or chemical reactions induced electrochemically, mechanochemically, annealing, or by plasma, irradiation or sonic energy to obtain diamond nanoparticles with an enhanced ability to absorb ultraviolet radiation compared to their unmodified state.

11. The surface coating or colorant preparation according to claim 10, wherein the diamond nanoparticles are modified so as to scavenge free radicals.

12. The surface coating or colorant preparation according to claim 10, wherein the diamond nanoparticles comprise modified ultradispersed diamond particles to enhance absorption of UV radiation compared to their unmodified state by one or more of introduction of dopants or impurities or creation of defects, internal defects, structural defects, sp2 bonded surface termination, surface functional groups attached to the nanodiamond surface by covalent or non-covalent bonds, or diamond particles with attached organic molecules.

13. The surface coating or colorant preparation according to claim 12, wherein the diamond nanoparticles comprise diamond nanoparticles having surface modifications of oxygen-containing surface groups.

14. The surface coating or colorant preparation according to claim 1, wherein the curable binding matrix is selected from the group consisting of: a polymer matrix, an epoxy, polytetrafluoroethelyne, resins, polycarbonates and polycarbonate blends, polystyrene, polyurethanes, polyimides, acrylics, epoxies, methacrylic, phenolics, silicones, polyesters, polyester fibers, unsaturated polyesters, polyurethane foam (PUF), polybutylene terephthalate (PBT), polyamides, polyamide fibers, polyacetals, vinyl polymers, phenol formaldehyde, neoprene, rubber, silicone rubber compounds, polypyrroles, polyaniline, polyacetylenes, polythiophenes, poly-p-phenylenes, polyacrylthiophenes, poly-p-phenylene-benzo-biz-thiozole (PBT), polymethylmethacrylate, butadieneacrylonitrile, fibers, ceramics, glasses, polyethyelene compounds with polyisobutylene, ethylene ethyl acrylate copolymers, extruded polystyrene foam, and expanded polyvinylchloride.

15. The surface coating or colorant preparation according to claim 1, wherein the curable binding matrix containing the UV radiation attenuating diamond nanoparticles further comprises a solvent in a concentration that renders the viscosity of the dispersion suitable for application as a surface coating using at least one of an aerosol spray process, an electrostatic spray process, a hot melt spray process, a high velocity high temperature spray process, a thermal spray process, an ultrasonic spray process, a fluidized bed process, a dipping process, a brushing process, a spin-on process, a wipe-on process, a plasma spraying process, a casting process, a molding process or an injection molding process.

16. An article coated by the surface coating or colorant preparation of claim 1.

17. The surface coating or colorant preparation according to claim 1, where the diamond nanoparticles have a size small enough to be substantially invisible to the naked eye, and where the diamond particles provide ultraviolet radiation degradation resistance properties in the dispersion, but where the amount of diamond nanoparticles are in a low enough concentration to be substantially invisible to the naked eye.

18. The surface coating or colorant preparation according to claim 17, further comprising a pigment that renders coloration to the surface coating or colorant preparation.

19. The surface coating or colorant preparation according to claim 17, further comprising a solvent to the material of the curable binding matrix.

20. The surface coating or colorant preparation according to claim 17, wherein the diamond nanoparticles having size greater than about 60 nn have a size of approximately 60-150 nm.

21. The surface coating or colorant preparation according to claim 17, wherein the diamond nanoparticles having size greater than about 60 nn have a size of approximately 100 nm.

22. The surface coating or colorant preparation according to claim 17, wherein the diamond nanoparticles comprise up to 25.0 percent by weight of the surface coating or colorant.

23. The surface coating or colorant preparation according to claim 17, wherein the diamond nanoparticles comprise between about 0.5 and 5.0 percent by weight of the preparation.

24. The surface coating or colorant preparation according to claim 1, wherein the diamond nanoparticles further comprise a mixture of nanodiamond particles with organic and/or inorganic UV absorbers, light stabilizers, or antioxidant agents, or any combination thereof.

25. The surface coating or colorant preparation according to claim 1, wherein the surface coating or colorant preparation is enclosed between two support structures.

26. A paint or surface coating preparation that provides resistance to degradation when exposed to at least some portion of ultraviolet radiation having wavelengths between approximately 190 and 400 nm comprising:
   a paint or surface coating preparation including a pigment, a curable binder, and a solvent to the pigment or the curable binder;
   a dispersion of an amount of diamond nanoparticles in the paint or surface coating preparation;
   wherein a plurality of the diamond nanoparticles comprise ultradispersed diamond particles; and
   wherein the diamond nanoparticles have a size greater than about 60 nm so that the diamond particles provide ultraviolet radiation degradation resistance properties in the dispersion.

27. The paint or surface coating preparation according to claim 26, wherein the diamond nanoparticles having size greater than about 60 nn have a size of approximately 60-150 nm.

28. The paint or surface coating preparation according to claim 26, wherein the diamond nanoparticles having size greater than about 60 nn have a size of approximately 100 nm.

29. The paint or surface coating preparation according to claim 26, wherein the diamond nanoparticles comprise up to 25.0 percent by weight of the surface coating or colorant.

30. The paint or surface coating preparation according to claim 26, wherein the nanodiamond particles have a visible color, and wherein the diamond nanoparticles impart a color to or modify a color of the dispersion.

31. The paint or surface coating preparation according to claim 26, wherein the diamond nanoparticles comprise modified diamond nanoparticles as a result of mechanochemical modification, annealing, or by plasma, irradiation or sonic energy or modified during a process of nanodiamond synthesis by introducing dopants and defects to obtain diamond nanoparticles with an enhanced ability to absorb ultraviolet radiation compared to their unmodified state.

32. An article coated by the paint or surface coating preparation of claim 26.

33. The paint or surface coating preparation according to claim 26, wherein the diamond nanoparticles comprise diamond nanoparticles modified by wet or gas phase chemical reactions, or chemical reactions induced electrochemically.

34. A surface coating or colorant preparation that provides resistance to degradation when exposed to at least some portion of ultraviolet radiation having wavelengths between approximately 190 and 400 nm comprising: a dispersion of an amount of diamond nanoparticles in a cured binding matrix that resides on a surface, wherein a plurality of the diamond nanoparticles comprise ultradispersed diamond nanoparticles having a size greater than about 60 nm so that the diamond nanoparticles provide ultraviolet radiation degradation resistance properties in the dispersion.

35. A surface coating or colorant preparation, comprising:
   curable binder material comprising a surface finish selected from the group consisting of: paint, varnish, finishing oil, shellac, plastic and polymer surface finish;
   a quantity of ultradispersed diamond nanoparticles dispersed in the curable binder material in an amount to provide attenuation of at least some portion of ultraviolet radiation having wavelengths between approximately 190 and 400 nm;
   where the curable binder material, when cured, has a binder thickness;
   where the curable binder material carries a distribution of the diamond nanoparticles throughout the binder thickness of the curable binder material when the binder material is cured;
   where the diamond nanoparticles have a size greater than about 60 nm;
   where the thickness of the curable binder material is greater than the thickness of the diamond nanoparticles when the curable binder material is cured; and
   where the diamond nanoparticles comprise diamond nanoparticles having defects or surface modifications that absorb ultraviolet radiation having wavelengths between approximately 190 and 400 nm.

36. The surface coating or colorant preparation according to claim 35, where at least a portion of the diamond nanoparticles comprise luminescent diamond nanoparticles dispersed in the curable binder material in an amount to provide attenuation of at least some portion of ultraviolet radiation having wavelengths between approximately 190 and 400 nm; and
   where the luminescent diamond nanoparticles absorb ultraviolet radiation having wavelengths between approximately 190 and 400 nm.

37. The surface coating or colorant preparation according to claim 35, where the diamond nanoparticles comprise diamond nanoparticles having surface modifications; and
   where the surface modification comprise oxygen or amine functional groups that absorb ultraviolet radiation having wavelengths between approximately 190 and 400 nm.

38. A surface coating or colorant preparation, comprising:
   a curable binder material comprising;
   a quantity of diamond nanoparticles dispersed in the curable binder material in an amount to provide attenuation of at least some portion of ultraviolet radiation having wavelengths between approximately 190 and 400 nm;
   where the diamond nanoparticles have a size greater than about 60 nm;
   where the curable binder material, when cured, has a binder thickness that is greater than the size of the diamond nanoparticles when the curable binder material is cured; and
   where the curable binder material carries a distribution of the diamond nanoparticles throughout the binder thickness of the binder material when the binder material is cured.

39. A surface coating or colorant preparation that provides resistance to degradation when exposed to at least some portion of ultraviolet radiation having wavelengths between approximately 190 and 400 nm comprising: a dispersion of an amount of diamond nanoparticles in a curable binding matrix, wherein a plurality of the diamond nanoparticles comprise ultradispersed diamond nanoparticles and a plurality of the diamond nanoparticles have a size greater than about 60 nm so that the diamond nanoparticles provide ultraviolet radiation degradation resistance properties when dispersed in the curable binding matrix and where the curable binding matrix comprises a material that cures to a solid film that adheres to a surface.

* * * * *